US012678338B2

(12) United States Patent
Hartwell et al.

(10) Patent No.: US 12,678,338 B2
(45) Date of Patent: *Jul. 14, 2026

(54) TISSUE HEALING

(71) Applicant: Smith & Nephew PLC, Watford (GB)

(72) Inventors: Samantha Dawn Hartwell, Hull (GB);
Donald Anthony Hudson, Claremont (ZA)

(73) Assignee: Smith & Nephew PLC, Watford (GB)

( * ) Notice: Subject to any disclaimer, the term of this patent is extended or adjusted under 35 U.S.C. 154(b) by 119 days.

This patent is subject to a terminal disclaimer.

(21) Appl. No.: 17/565,013

(22) Filed: Dec. 29, 2021

(65) Prior Publication Data

US 2022/0192886 A1     Jun. 23, 2022

Related U.S. Application Data

(63) Continuation of application No. 16/357,158, filed on Mar. 18, 2019, now Pat. No. 11,246,757, which is a
(Continued)

(30) Foreign Application Priority Data

May 17, 2011     (GB) ...................................... 1108229

(51) Int. Cl.
  *A61F 13/0246*     (2024.01)
  *A61F 13/02*     (2024.01)
  (Continued)

(52) U.S. Cl.
  CPC ...... *A61F 13/0253* (2013.01); *A61F 13/0206* (2013.01); *A61F 13/022* (2013.01);
  (Continued)

(58) Field of Classification Search
  CPC .............. A61F 13/0253; A61F 13/0206; A61F 13/022; A61F 13/0223; A61F 13/0243;
  (Continued)

(56) References Cited

U.S. PATENT DOCUMENTS

| | | | | |
|---|---|---|---|---|
| 3,459,618 A | * | 8/1969 | Egler ................ | A61F 13/15731 156/219 |
| 3,645,835 A | | 2/1972 | Hodgson | |

(Continued)

FOREIGN PATENT DOCUMENTS

| | | | |
|---|---|---|---|
| DE | 3443101 A1 | 5/1986 | |
| DE | 202004017052 U1 | 6/2005 | |

(Continued)

OTHER PUBLICATIONS

Worley, Cynthia A. "So, what do I put on this wound? The wound dressing puzzle: part III." Dermatol Nurs 17 (2005): 299-300. (Year: 2005).*

(Continued)

*Primary Examiner* — Adam Marcetich

(74) *Attorney, Agent, or Firm* — Knobbe, Martens, Olson & Bear, LLP

(57) ABSTRACT

A system, method, and apparatus are disclosed for dressing a wound and for minimizing scarring. The apparatus promotes scar-minimizing healing of a wound where negative pressure wound therapy is applied, and comprises a wound contact layer containing silicone, polysiloxanes, or other related compounds.

17 Claims, 11 Drawing Sheets

Related U.S. Application Data continuation of application No. 14/118,202, filed as application No. PCT/GB2011/001553 on Nov. 2, 2011, now Pat. No. 10,231,878.

(51) Int. Cl.

| | |
|---|---|
| *A61F 13/0203* | (2024.01) |
| *A61F 13/0206* | (2024.01) |
| *A61F 13/05* | (2024.01) |
| *A61M 1/00* | (2006.01) |

(52) U.S. Cl.
CPC ...... *A61F 13/0223* (2013.01); *A61F 13/0243* (2013.01); *A61F 13/05* (2024.01); *A61M 1/915* (2021.05); *A61M 1/985* (2021.05); *A61M 1/916* (2021.05)

(58) Field of Classification Search
CPC ...... A61F 13/05; A61F 13/02; A61F 13/0246; A61F 2013/00859; A61F 2013/00863; A61F 2013/00868; A61F 2013/00872; A61F 2013/00876; A61F 13/0226; A61F 13/025; A61F 13/01046; A61M 1/915; A61M 1/916; A61M 2205/7536
See application file for complete search history.

(56) References Cited

U.S. PATENT DOCUMENTS

| | | | |
|---|---|---|---|
| 3,908,650 A | 9/1975 | Dunshee et al. | |
| 3,972,328 A | 8/1976 | Chen | |
| 4,029,598 A | 6/1977 | Neisius et al. | |
| 4,595,001 A | 6/1986 | Potter et al. | |
| 4,728,499 A | 3/1988 | Fehder | |
| 4,743,249 A | 5/1988 | Loveland | |
| 4,798,201 A | 1/1989 | Rawlings et al. | |
| 4,813,942 A | 3/1989 | Alvarez | |
| 5,010,883 A | 4/1991 | Rawlings et al. | |
| 5,056,510 A | 10/1991 | Gilman | |
| 5,181,905 A | 1/1993 | Flam | |
| 5,238,732 A | 8/1993 | Krishnan | |
| 5,340,363 A | 8/1994 | Fabo | |
| 5,549,584 A | 8/1996 | Gross | |
| 5,641,506 A | 6/1997 | Talke et al. | |
| 5,707,499 A | 1/1998 | Joshi et al. | |
| 5,759,570 A | 6/1998 | Arnold | |
| 5,852,126 A | 12/1998 | Barnard et al. | |
| 5,910,125 A | 6/1999 | Cummings et al. | |
| 6,071,267 A | 6/2000 | Zamierowski | |
| 6,277,224 B1 | 8/2001 | Muesch et al. | |
| 6,345,623 B1 | 2/2002 | Heaton et al. | |
| 6,495,229 B1 | 12/2002 | Carte et al. | |
| 6,626,891 B2 | 9/2003 | Ohmstede | |
| 6,685,681 B2 | 2/2004 | Lockwood et al. | |
| 6,752,794 B2 | 6/2004 | Lockwood et al. | |
| 6,903,243 B1 | 6/2005 | Burton | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,070,584 B2 | 7/2006 | Johnson et al. | |
| 7,108,683 B2 | 9/2006 | Zamierowski | |
| 7,216,651 B2 | 5/2007 | Argenta et al. | |
| 7,361,184 B2 | 4/2008 | Joshi | |
| 7,381,859 B2 | 6/2008 | Hunt et al. | |
| 7,569,742 B2 | 8/2009 | Haggstrom et al. | |
| 7,605,298 B2 | 10/2009 | Bechert et al. | |
| 7,615,036 B2 | 11/2009 | Joshi et al. | |
| 7,622,629 B2 | 11/2009 | Aali | |
| 7,625,362 B2 | 12/2009 | Boehringer et al. | |
| 7,699,823 B2 | 4/2010 | Haggstrom et al. | |
| 7,700,819 B2 | 4/2010 | Ambrosio et al. | |
| 7,708,724 B2 | 5/2010 | Weston | |
| 7,718,249 B2 | 5/2010 | Russell et al. | |
| 7,722,582 B2 | 5/2010 | Lina et al. | |
| 7,749,531 B2 | 7/2010 | Booher | |
| 7,759,537 B2 | 7/2010 | Bishop et al. | |
| 7,759,539 B2 | 7/2010 | Shaw et al. | |
| 7,775,998 B2 | 8/2010 | Riesinger | |
| 7,779,625 B2 | 8/2010 | Joshi et al. | |
| 7,811,269 B2 | 10/2010 | Boynton et al. | |
| 7,838,717 B2 | 11/2010 | Haggstrom et al. | |
| 7,846,141 B2 | 12/2010 | Weston | |
| 7,910,791 B2 | 3/2011 | Coffey | |
| 7,922,703 B2 | 4/2011 | Riesinger | |
| 7,959,624 B2 | 6/2011 | Riesinger | |
| 7,964,766 B2 | 6/2011 | Blott et al. | |
| 7,976,519 B2 | 7/2011 | Bubb et al. | |
| 8,034,037 B2 | 10/2011 | Adams et al. | |
| 8,062,272 B2 | 11/2011 | Weston | |
| 8,062,331 B2 | 11/2011 | Zamierowski | |
| 8,080,702 B2 | 12/2011 | Blott et al. | |
| 8,118,794 B2 | 2/2012 | Weston | |
| 8,152,785 B2 | 4/2012 | Vitaris | |
| 8,162,907 B2 | 4/2012 | Heagle | |
| 8,207,392 B2 | 6/2012 | Haggstrom et al. | |
| 8,235,972 B2 | 8/2012 | Adahan | |
| 8,241,261 B2 | 8/2012 | Randolph et al. | |
| 8,282,611 B2 | 10/2012 | Weston | |
| 8,303,552 B2 | 11/2012 | Weston | |
| 8,372,049 B2 | 2/2013 | Jaeb et al. | |
| 8,372,050 B2 | 2/2013 | Jaeb et al. | |
| 8,425,478 B2 | 4/2013 | Olson | |
| 8,444,612 B2 | 5/2013 | Patel et al. | |
| 8,460,255 B2 | 6/2013 | Joshi et al. | |
| 8,540,688 B2 | 9/2013 | Eckstein et al. | |
| 8,545,466 B2 | 10/2013 | Andresen et al. | |
| 8,568,386 B2 | 10/2013 | Malhi | |
| 8,628,505 B2 | 1/2014 | Weston | |
| 8,641,691 B2 | 2/2014 | Fink et al. | |
| 8,663,198 B2 | 3/2014 | Buan et al. | |
| 8,715,256 B2 | 5/2014 | Greener | |
| 8,764,732 B2 | 7/2014 | Hartwell | |
| 8,777,911 B2 * | 7/2014 | Heagle | A61M 1/98 604/317 |
| 8,795,243 B2 | 8/2014 | Weston | |
| 8,795,800 B2 | 8/2014 | Evans | |
| 8,808,274 B2 | 8/2014 | Hartwell | |
| 8,829,263 B2 | 9/2014 | Haggstrom et al. | |
| 8,834,451 B2 | 9/2014 | Blott et al. | |
| 8,834,452 B2 | 9/2014 | Hudspeth et al. | |
| 8,956,336 B2 | 2/2015 | Haggstrom et al. | |
| 9,061,095 B2 | 6/2015 | Adie et al. | |
| 9,067,003 B2 | 6/2015 | Buan et al. | |
| 9,127,665 B2 | 9/2015 | Locke et al. | |
| 9,168,330 B2 | 10/2015 | Joshi et al. | |
| 9,199,012 B2 | 12/2015 | Vitaris et al. | |
| 9,220,822 B2 | 12/2015 | Hartwell | |
| 9,283,118 B2 | 3/2016 | Locke et al. | |
| 9,302,033 B2 | 4/2016 | Riesinger | |
| 9,375,353 B2 | 6/2016 | Vitaris et al. | |
| 9,375,521 B2 | 6/2016 | Hudspeth et al. | |
| 9,381,283 B2 | 7/2016 | Adams et al. | |
| 9,452,248 B2 | 9/2016 | Blott et al. | |
| 9,474,654 B2 * | 10/2016 | Heagle | A61F 13/01042 |
| 9,597,489 B2 | 3/2017 | Heagle | |
| 9,669,138 B2 | 6/2017 | Joshi et al. | |
| 9,682,179 B2 | 6/2017 | May | |
| 9,795,725 B2 | 10/2017 | Joshi et al. | |
| 9,808,561 B2 | 11/2017 | Adie et al. | |
| 9,844,475 B2 * | 12/2017 | Hartwell | A61F 13/05 |
| 9,907,703 B2 * | 3/2018 | Allen | A61M 1/985 |
| 9,956,121 B2 * | 5/2018 | Hartwell | A61M 1/985 |
| 10,123,909 B2 * | 11/2018 | Hartwell | A61F 13/05 |
| 11,129,751 B2 * | 9/2021 | Hartwell | A61F 13/0226 |
| 2001/0020146 A1 | 9/2001 | Satterfield et al. | |
| 2002/0082567 A1 | 6/2002 | Lockwood et al. | |
| 2003/0125646 A1 | 7/2003 | Whitlock | |
| 2004/0057855 A1 | 3/2004 | Gerlach et al. | |
| 2004/0126413 A1 | 7/2004 | Sigurjonsson et al. | |
| 2005/0154340 A1 | 7/2005 | Schlussel | |
| 2006/0009744 A1 | 1/2006 | Erdman et al. | |
| 2006/0079852 A1 | 4/2006 | Bubb et al. | |

(56) References Cited

U.S. PATENT DOCUMENTS

| | | | |
|---|---|---|---|
| 2007/0040454 A1 | 2/2007 | Freudenberger et al. |
| 2007/0055209 A1 | 3/2007 | Patel et al. |
| 2007/0225663 A1 | 9/2007 | Watt et al. |
| 2007/0255194 A1 | 11/2007 | Gudnason et al. |
| 2008/0031748 A1 | 2/2008 | Ihle et al. |
| 2008/0132821 A1 | 6/2008 | Propp et al. |
| 2008/0167593 A1 | 7/2008 | Fleischmann |
| 2008/0223378 A1 | 9/2008 | Henderson et al. |
| 2008/0233348 A1 | 9/2008 | Ishiwatari et al. |
| 2008/0255493 A1 | 10/2008 | Sigurjonsson et al. |
| 2008/0306456 A1 | 12/2008 | Riesinger |
| 2009/0125004 A1 | 5/2009 | Shen et al. |
| 2009/0157024 A1 | 6/2009 | Song |
| 2009/0192475 A1 | 7/2009 | Siegel |
| 2009/0216170 A1 | 8/2009 | Robinson et al. |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0254053 A1 | 10/2009 | Svensby et al. |
| 2009/0299251 A1 | 12/2009 | Buan |
| 2009/0299306 A1 | 12/2009 | Buan |
| 2010/0030170 A1 | 2/2010 | Keller et al. |
| 2010/0030178 A1 | 2/2010 | Macmeccan et al. |
| 2010/0125258 A1 | 5/2010 | Coulthard et al. |
| 2010/0159192 A1 | 6/2010 | Cotton |
| 2010/0179463 A1 | 7/2010 | Greener et al. |
| 2010/0210986 A1 | 8/2010 | Sanders et al. |
| 2010/0259406 A1 | 10/2010 | Caso et al. |
| 2010/0262090 A1 | 10/2010 | Riesinger |
| 2010/0262091 A1 | 10/2010 | Larsson |
| 2010/0268198 A1 | 10/2010 | Buan et al. |
| 2010/0305490 A1 | 12/2010 | Coulthard et al. |
| 2010/0305526 A1 | 12/2010 | Robinson et al. |
| 2010/0318052 A1 | 12/2010 | Ha et al. |
| 2010/0324510 A1 | 12/2010 | Andresen et al. |
| 2011/0004172 A1 | 1/2011 | Eckstein et al. |
| 2011/0028918 A1 | 2/2011 | Hartwell |
| 2011/0028919 A1 | 2/2011 | Johnnison et al. |
| 2011/0033515 A1 | 2/2011 | Harpstead et al. |
| 2011/0054421 A1 | 3/2011 | Hartwell |
| 2011/0054422 A1 | 3/2011 | Locke et al. |
| 2011/0112492 A1* | 5/2011 | Bharti ..................... A61F 13/05 604/319 |
| 2011/0118683 A1 | 5/2011 | Weston |
| 2011/0160686 A1 | 6/2011 | Ueda et al. |
| 2011/0172612 A1 | 7/2011 | Greener et al. |
| 2011/0224631 A1 | 9/2011 | Simmons et al. |
| 2011/0257572 A1 | 10/2011 | Locke et al. |
| 2011/0282309 A1 | 11/2011 | Adie et al. |
| 2012/0029455 A1 | 2/2012 | Perez-Foullerat et al. |
| 2012/0041399 A1 | 2/2012 | Blott et al. |
| 2012/0041402 A1 | 2/2012 | Greener |
| 2012/0051945 A1 | 3/2012 | Orndorff et al. |
| 2012/0058289 A1 | 3/2012 | Coates et al. |
| 2012/0095380 A1 | 4/2012 | Gergely et al. |
| 2012/0123220 A1* | 5/2012 | Lyer ........................ A61L 15/58 156/767 |
| 2012/0232502 A1 | 9/2012 | Lowing |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0116635 A1 | 5/2013 | Fleischmann |
| 2013/0138054 A1 | 5/2013 | Fleischmann |
| 2013/0138060 A1 | 5/2013 | Haggstrom et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0274688 A1 | 10/2013 | Weston |
| 2013/0296762 A1 | 11/2013 | Toth |
| 2013/0302545 A1 | 11/2013 | Schnelker et al. |
| 2013/0331822 A1 | 12/2013 | Patel et al. |
| 2013/0338613 A1 | 12/2013 | Haggstrom et al. |
| 2014/0058309 A1 | 2/2014 | Addison et al. |
| 2014/0114268 A1 | 4/2014 | Auguste et al. |

| | | | |
|---|---|---|---|
| 2014/0142524 A1 | 5/2014 | Eckstein et al. |
| 2014/0228791 A1 | 8/2014 | Hartwell |
| 2014/0236109 A1 | 8/2014 | Greener |
| 2014/0249493 A1 | 9/2014 | Hartwell |
| 2014/0316359 A1 | 10/2014 | Collinson et al. |
| 2014/0350494 A1 | 11/2014 | Hartwell et al. |
| 2015/0032035 A1 | 1/2015 | Banwell et al. |
| 2015/0065965 A1 | 3/2015 | Haggstrom et al. |
| 2015/0209492 A1 | 7/2015 | Blott et al. |
| 2015/0308994 A1 | 10/2015 | Hammond et al. |
| 2015/0320605 A1 | 11/2015 | Pigg et al. |
| 2016/0081859 A1 | 3/2016 | Hartwell |
| 2016/0144084 A1 | 5/2016 | Collinson et al. |
| 2016/0298620 A1 | 10/2016 | Cordoba et al. |
| 2016/0317357 A1 | 11/2016 | Vitaris et al. |
| 2017/0128642 A1 | 5/2017 | Buan |
| 2017/0181896 A1 | 6/2017 | Hartwell |
| 2017/0181897 A1 | 6/2017 | Hartwell |
| 2017/0348154 A1 | 12/2017 | Robinson et al. |

FOREIGN PATENT DOCUMENTS

| | | | |
|---|---|---|---|
| EP | 0257916 A1 | 3/1988 |
| EP | 0300620 A1 | 1/1989 |
| EP | 0340018 A2 | 11/1989 |
| EP | 1476217 B1 | 3/2008 |
| EP | 1955887 A2 | 8/2008 |
| EP | 2021046 B1 | 3/2012 |
| EP | 2462908 A1 | 6/2012 |
| EP | 2544642 B1 | 1/2015 |
| EP | 2648668 A4 | 1/2015 |
| EP | 2830555 A1 | 2/2015 |
| EP | 2836711 A1 | 2/2015 |
| EP | 2837370 A1 | 2/2015 |
| EP | 3628289 B1 | 11/2021 |
| FR | 1163907 A | 10/1958 |
| FR | 2633825 A1 | 1/1990 |
| GB | 1255395 A | 12/1971 |
| GB | 2307180 B | 6/2000 |
| GB | 2468905 A | 9/2010 |
| JP | 2010000159 A | 1/2010 |
| WO | WO-8300742 A1 | 3/1983 |
| WO | WO-9216245 A1 | 10/1992 |
| WO | WO-9420041 A1 | 9/1994 |
| WO | WO-9529959 A1 | 11/1995 |
| WO | WO-9605873 A1 | 2/1996 |
| WO | WO-2004006972 A1 | 1/2004 |
| WO | WO-2004060225 A1 | 7/2004 |
| WO | WO-2004060359 A1 | 7/2004 |
| WO | WO-2004077387 A1 | 9/2004 |
| WO | WO-2004108175 A1 | 12/2004 |
| WO | WO-2005025447 A2 | 3/2005 |
| WO | WO-2005046760 A1 | 5/2005 |
| WO | WO-2005051461 A1 | 6/2005 |
| WO | WO-2005105180 A1 | 11/2005 |
| WO | WO-2005123170 A1 | 12/2005 |
| WO | WO-2006052839 A2 | 5/2006 |
| WO | WO-2006133430 A2 | 12/2006 |
| WO | WO-2008039223 A1 | 4/2008 |
| WO | WO-2008109887 A1 | 9/2008 |
| WO | WO-2009066105 A1 | 5/2009 |
| WO | WO-2009082486 A1 | 7/2009 |
| WO | WO-2009124100 A1 | 10/2009 |
| WO | WO-2009146441 A1 | 12/2009 |
| WO | WO-2009147402 A2 | 12/2009 |
| WO | WO-2009158128 A2 | 12/2009 |
| WO | WO-2010061228 A1 | 6/2010 |
| WO | WO-2010122665 A1 | 10/2010 |
| WO | WO-2010142959 A2 | 12/2010 |
| WO | WO-2010147533 A1 | 12/2010 |
| WO | WO-2010147930 A1 | 12/2010 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2012028842 A1 | 3/2012 |
| WO | WO-2012034238 A1 | 3/2012 |
| WO | WO-2012041296 A2 | 4/2012 |
| WO | WO-2012131237 A1 | 10/2012 |

(56) References Cited

FOREIGN PATENT DOCUMENTS

| WO | WO-2012140378 A1 | 10/2012 |
| WO | WO-2012143665 A1 | 10/2012 |
| WO | WO-2012156655 A1 | 11/2012 |
| WO | WO-2013010907 A1 | 1/2013 |
| WO | WO-2013064852 A1 | 5/2013 |
| WO | WO-2013083800 A1 | 6/2013 |
| WO | WO-2013090810 A1 | 6/2013 |
| WO | WO-2013114097 A1 | 8/2013 |
| WO | WO-2013136181 A2 | 9/2013 |
| WO | WO-2013149078 A1 | 10/2013 |
| WO | WO-2014008348 A2 | 1/2014 |
| WO | WO-2014016759 A1 | 1/2014 |
| WO | WO-2014020440 A1 | 2/2014 |
| WO | WO-2014020443 A2 | 2/2014 |
| WO | WO-2014108476 A1 | 7/2014 |
| WO | WO-2014113253 A1 | 7/2014 |
| WO | WO-2014184674 A2 | 11/2014 |
| WO | WO-2015022334 A1 | 2/2015 |
| WO | WO-2015022340 A1 | 2/2015 |
| WO | WO-2015031216 A1 | 3/2015 |
| WO | WO-2015052225 A1 | 4/2015 |

OTHER PUBLICATIONS

Cubison, T. C., Pape, S. A., & Parkhouse, N. (2006). Evidence for the link between healing time and the development of hypertrophic scars (HTS) in paediatric burns due to scald injury. Burns, 32(8), 992-999.*
Wilkinson, H. N., Longhorne, F. L., Roberts, E. R., Brownhill, V. R., & Hardman, M. J. (2021). Cellular benefits of single-use negative pressure wound therapy demonstrated in a novel ex vivo human skin wound model. Wound Repair and Regeneration, 29(2), 298-305.*
SSPM823 Thin Silicone Membranes—Specialty Silicone Products, SSPM823 Rev. 5, Nov. 24, 2014. https://sspinc.com/products/sspm823/.*
Benedek I., et al., "Technology of Pressure Sensitive Adhesives and Products," Chapter 6, 2009, 25 pages.
Communication indication Deficiencies in the Notice of Opposition for European Patent No. 2712312, dated Sep. 21, 2023, 6 pages.
Communication of a Notice of Opposition including Statement of Facts and Arguments for European Patent No. 2712312, dated Sep. 19, 2023, 18 pages.
Decision of Board of Appeal T 0555/18 Datasheet for the decision of Sep. 14, 2022 for European Patent No. 2117839, mailed on Oct. 26, 2022, 22 pages.
Declaration of Akagi Keiji for European Patent No. 2712312 dated Oct. 6, 2023, 1 page.
KCI, "V.A.C. Therapy Clinical guidelines: A reference source for clinicians," Jan. 2005, 36 pages.
Letter from Opponent regarding the Opposition Procedure for European Patent No. 2712312, dated Sep. 22, 2023, 3 pages.
Mustoe T.A., "Evolution of Silicone Therapy and Mechanism of Action in Scar Management", Aesth Plast Surg 2008, 32:82-92, 11 Pages.
Notice of Opposition—Opponent's Statement of Facts and Arguments of the European Patent No. 2712312, dated Oct. 9, 2023, 12 pages.
Notice of Opposition—Opponent's Statement of Facts and Arguments of the European Patent No. 2712312, dated Oct. 13, 2023, 29 pages.
Notice of Opposition—Opponent's Statement of Facts and Arguments of the European Patent No. 2712312, dated Oct. 16, 2023, 33 pages.
Notice of Opposition—Opponent's Statement of Facts and Arguments of the European Patent No. 2712312, dated Oct. 17, 2023, 66 pages.
Wikipedia: "Silicone Gel Sheeting", Sep. 28, 2023, 8 Pages, Retrieved from the Internet: URL: https://en.wikipedia.org/wiki/Silicone_gel_sheeting.

BASF., "Thermoplastic Polyurethane Elastomers (TPU)," Elastollan—Product Range, 2016, 40 pages, Retrieved from the Internet: URL: https://www.basf.com/kr/documents/ko/product/Thermoplastic%20Polyurethane_Elastollan_Product%20Range.pdf.
Abaev J.K., "Handbook of the surgeon, Wounds and wound infection," Rostov-on-Don, Phoenix, 2006, 433 pages.
Acton C., "Use of Mepitel One in Conjunction with Negative Pressure Wound Therapy: A Case Study Series," 2009, 1 page.
Advantec MFS, Inc., "Membrane Filters" (catalog), retrieved from http://www.advantecmfs.com/catalog/filt/membrane.pdf, on Jan. 29, 2016, Copyright 2001-2011, 17 pages.
Atiyeh B.S., "Nonsurgical Management of Hypertrophic Scars: Evidence-Based Therapies, Standard Practices, and Emerging Methods," Aesthetic Plastic Surgery, vol. 31, No. 5, 2007, pp. 468-492.
Blakely A.M., "The Innovative Use of Safetac® Soft Silicone in Conjunction with Negative Pressure Wound Therapy: Three Case Studies," 2007, 1 page.
Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.
International Preliminary Report on Patentability for Application No. PCT/GB2011/001553, mailed on Nov. 28, 2013, 11 pages.
International Search Report and Written Opinion for Application No. PCT/GB2011/001553, mailed on Apr. 12, 2012, 14 pages.
Jones S.M., et al., "Interface Dressings Influence the Delivery of Topical Negative-Pressure Therapy," Plastic and Reconstructive Surgery, Sep. 15, 2005, 6 pages.
Kendall ULTEC Hydrocolloid Dressing (4×4"), Product Ordering Page, web page downloaded on Jul. 13, 2014, 1 page.
Protz K., "Modern Wound Dressings Support the Healing Process," Wound care: Indications and Application, Geriatrie Journal, Apr. 2005, pp. 3333-3339 (17 pages with English translation).
Smith & Nephew, "PICO Single Use Negative Pressure Wound Therapy System," Spiral Booklet, Mar. 2011, 7 pages.
Technology Watch, May 1989, 1 page.
Brief Communication—Letter from the Opponent O2 of Jun. 18, 2024 for European Patent No. 2712312, mailed on Jun. 21, 2024, 17 pages.
Brief Communication—Letter from the Opponent O4 of Jun. 4, 2024 for European Patent No. 2712312, mailed on Jun. 7, 2024, 4 pages.
Brief Communication—Letter from the Proprietor of the Patent of Mar. 4, 2024 for European Patent No. 2712312, mailed Mar. 11, 2024, 33 pages.
Brief Communication—Letter from the Proprietor of the Patent of Mar. 12, 2024 for European Patent No. 2712312, mailed Mar. 15, 2024, 3 pages.
Declaration of Dr. Viktoria Skeppstedt filed in the Opposition against European Patent No. 2712312, dated Jun. 13, 2024, 2 pages.
Declaration of Victoria Beadle filed in the Opposition against European Patent No. 2712312, dated Mar. 1, 2024, 3 pages.
Letter from Opponent regarding the Opposition Procedure for European Patent No. 2712312, dated Mar. 20, 2024, 4 pages.
Notice of Communication of Amended Entries concerning the Representative (R. 143(1)(h) EPC) for European Patent No. 2712312, mailed on Mar. 6, 2024, 39 pages.
Study Record of "PICO Breast Reduction Clinical Study Looking at Incision Healing Complications", Smith & Nephew, Inc. (sponsor), ClinicalTrials.gov ID: NCT01640366, last update posted Feb. 28, 2020, 8 pages. URL: https://clinicaltrials.gov/study/NCT01640366.
Brief Communication—Letter from the Proprietor of the Patent of Oct. 14, 2024 for European Patent No. 2712312, mailed Oct. 18, 2024, 6 pages.
Brownhill, V. et al., "Pre-Clinical Assessment of Single-Use Negative Pressure Wound Therapy During In Vivo Porcine Wound Healing", Advances in Wound Care, 2020, vol. 00, No. 00, in 12 pages.
Declaration under 37 C.F.R. 1.132 of Samantha Dawn Hartwell dated Jul. 25, 2024, 11 pages.
"Unlocking the mechanism of action (MoA) of PICO Single Use Negative Wound Pressure Therapy System (sNPWT)", Smith+Nephew, 2021, AWM-AWD-29707 | GMC1352, in 36 pages.

(56) References Cited

OTHER PUBLICATIONS

Annex to the Communication filed in the Opposition against European Patent No. 2712312, mailed on Dec. 3, 2024, 19 pages.
Baraboski S., et al., "Wound Care Essentials: Practice Principles," Lippincott Williams & Wilkins, 2004, 3 pages.
Brief Communication—Letter from the Opponent O1 of Aug. 8, 2025 filed in the Opposition against European Patent No. 2712312, dated Aug. 12, 2025, 10 pages.
Brief Communication—Letter from the Opponent O2 of Aug. 8, 2025 filed in the Opposition against European Patent No. 2712312, dated Aug. 13, 2025, 18 pages.
Brief Communication—Letter from the Opponent O3 of Aug. 8, 2025 filed in the Opposition against European Patent No. 2712312, dated Aug. 13, 2025, 18 pages.
Brief Communication—Letter from the Opponent O4 of Aug. 8, 2025 filed in the Opposition against European Patent No. 2712312, dated Aug. 13, 2025, 10 pages.
Brief Communication—Letter from the proprietor of the patent of Aug. 8, 2025 filed in the Opposition against European Patent No. 2712312, mailed on Aug. 14, 2025, 5 pages.
Decision of Board of Appeal T 2401/19 Datasheet for the decision of Feb. 5, 2024, 51 pages.
Declaration II of Viktoria Skeppstedt filed in the Opposition against European Patent No. 2712312, dated Jul. 1, 2025, 2 pages.
Markers of Wound Bed Inflammation, filed in the Opposition against European Patent No. 2712312 on Aug. 8, 2025, 2 pages.
Declaration of Dr. Maria Skold filed in the Opposition against European Patent No. 2712312, dated Mar. 2, 2026, 4 pages.
Statement of Grounds of Appeal against European Patent No. 2712312, mailed on Mar. 4, 2026, 21 pages.
Statement of Grounds of Appeal for European Patent No. 2712312, mailed on Mar. 4, 2026, 9 pages.
Statement of Grounds of Appeal for European Patent No. 2712312, mailed on Mar. 6, 2026, 99 pages.

* cited by examiner

110

105 y 1001     1002

TISSUE HEALING

CROSS-REFERENCE TO RELATED APPLICATIONS

This application is a continuation of U.S. application Ser. No. 16/357,158, filed Mar. 18, 2019, which is a continuation of U.S. application Ser. No. 14/118,202, filed Jun. 26, 2014, now U.S. Pat. No. 10,231,878, which is a U.S. National Phase of the PCT International Application No. PCT/GB2011/001553, filed on Nov. 2, 2011, and which claims priority to UK Application No. 1108229.4, filed on May 17, 2011.

BACKGROUND OF THE INVENTION

Field of the Invention

Embodiments of the present invention relate to methods and apparatuses for promoting scar-free healing of tissue. In particular, but not exclusively, the embodiments of the present invention relate to an apparatus for promoting scar-free healing of a wound at a wound site where negative pressure wound therapy (NPWT) is applied.

Description of the Related Art

A scar has been defined as "fibrous connective tissue that forms at the site of injury or disease in any tissue of the body". Scarring may thus result from healing of a wound or through the deposition of scar tissue associated with certain fibrotic disorders.

Although the ill effects of scarring, whether resulting from wound healing or associated fibrotic disorders, are well-known there remains a lack of effective therapies able to partially or wholly reduce these effects.

For example, silicone scar treatments are often used for preventing scar formation and improving existing scar appearance. Also, pressure dressings are commonly used, particularly when managing burn or hypertrophic scars. In practice, improved performance in respect of both conventional techniques is desirable.

SUMMARY OF THE INVENTION

It is an aim of the present invention to at least partly mitigate the above-mentioned problem.

It is an aim of certain embodiments of the present invention to provide an apparatus and method for promoting scar-free healing of a wound where negative pressure wound therapy (NPWT) is applied.

It is an aim of certain embodiments of the present invention to provide a drug delivery system for providing an effective daily dose of silicone or its pharmaceutically acceptable equivalent by topical administration in the treatment of anti-scarring whereby a reduced level of scarring is experienced by a host relative to scarring expected from conventional wound dressing treatments.

It is an aim of certain embodiments of the present invention to provide a method and apparatus for promoting scar-free tissue at a wide variety of tissue sites where negative pressure therapy (NPT) is applied.

According to a first embodiment, there is provided apparatus for promoting scar-free healing of a wound at a wound site where negative pressure wound therapy (NPWT) is applied, the apparatus comprising:

a wound contact layer comprising silicone and an open area in an amount and proportion sufficient to inhibit scar tissue formation when NPWT is applied at the wound site.

According to a second embodiment, there is provided apparatus for promoting scar-free healing at a tissue site where negative pressure therapy (NPT) is applied, the apparatus comprising:

a tissue contact layer comprising silicone and an open area in an amount and proportion sufficient to reduce scar tissue when NPT is applied at the tissue site said scar tissue being associated with a fibrotic disorder.

According to a third embodiment, there is provided use of negative pressure wound therapy (NPWT) together with a wound dressing comprising a wound contact layer comprising silicone and an open area comprising around 20% or less of an overall area of the wound contact layer to thereby promote substantially scar-free healing of an incisional wound.

According to a fourth embodiment, there is provided a topical controlled drug delivery system comprising an effective daily dose of silicone or its pharmaceutically acceptable equivalent, by topical administration in combination with the application of negative pressure wound therapy (NPWT), to a host suffering from a wound, in the treatment of anti-scarring, wherein a reduced level of scarring is experienced by the host relative to conventional wound dressing treatments in the form of topical silicone holding gel dressings.

According to a fifth embodiment, there is provided a method for promoting scar-free healing at a tissue site where negative pressure therapy (NPT) is applied, the method comprising the steps of:

locating a wound dressing, comprising a tissue contact layer comprising silicone and an open area in an amount and proportion sufficient to at least reduce scar tissue when NPT is applied at the tissue site, at a tissue site;

applying NPT to the tissue site via the wound dressing; and at least reducing scar tissue at the tissue site.

According to a sixth embodiment, there is provided a method for the treatment of a wound, the method comprising the steps of:

providing a wound dressing comprising a silicone wound contact layer and a moisture vapor permeable cover layer;

positioning the dressing over a wound site to form a sealed cavity over the wound site; and applying negative pressure to the wound site so as to draw fluid from the wound site into the sealed cavity.

Certain embodiments of the present invention may provide for fluid from the wound to be contained in a sealed cavity in the wound dressing. Certain embodiments may provide for the scar tissue formation at the wound site to be reduced as compared to the scar tissue formation that would have occurred using a wound dressing without said silicone wound contact layer. For example, the scar tissue formation may be reduced by at least one point according to the Vancouver Scar Scale or Manchester Scar Scale. In some embodiments, leaking silicone from the wound contact layer to the wound site in an amount may be sufficient to reduce scar tissue formation.

Certain embodiments of the present invention provide the advantage that when a wound contact layer of a dressing located over a wound contains silicone and an open area which presents little open area to a lower wound, and when negative pressure therapy is applied via the dressing, then scar tissue formation is wholly or partially prevented or reduced.

Certain embodiments of the present invention can be utilised at any tissue site where scar tissue is extant or whether scar tissue formation is to be expected. By utilising negative pressure therapy in conjunction with a dressing including a tissue contact layer which includes silicone and which also has a limited open area scar material can be reduced or scar material can be inhibited from forming.

Certain embodiments of the present invention provide a methodology and apparatus able to dose a tissue site with silicone in an amount and proportion and via a technique which results in far less scarring than would otherwise be expected with conventional topically applied silicone dressings, ointments or pressure dressings.

Certain embodiments of the present invention provide a method and apparatus able to produce, in use, an increased static electric charge at an interface region between a dressing and underlying tissue. The interaction between the negatively charged ions and ionic charges of the tissue fluids and/or skin assists in the total or partial prevention of scar tissue formation or in scar reduction.

Certain embodiments of the present invention can be utilised with any type of scarring such as scars caused in surgery or in the amelioration of pre-existing scars. Depending upon a stage and maturity of scar tissue use can be selected so as to leave an improved skin surface in terms of cosmetic appeal as well as being more functional physiologically and mechanically.

Certain embodiments of the present invention enable silicone oil to leak from a silicone holding layer. In hand with a substantially occlusive layer this leads to a wound dressing which can provide substantial improvement in wound treatment.

Certain embodiments of the present invention provide a method and apparatus in which a silicone holding layer can limit moisture loss from an underlying skin surface and aid hydration. Also, a layer is provided which does not limit access of oxygen to the skin surface. Overall, scar formation is thus prevented or reduced.

Certain embodiments of the present invention may be used for cosmetic purposes.

Certain embodiments of the present invention enable the cotemporaneous application of compressive forces and adhesive forces and also provide a wound dressing which helps buffer external sheer forces at a tissue site. As a result, a particularly optimum environment is provided to assist in scar-free healing/tissue formation.

BRIEF DESCRIPTION OF THE DRAWINGS

Embodiments of the present invention will now be described hereinafter, by way of example only, with reference to the accompanying drawings in which.

In the drawings like reference numerals refer to like parts.

Figure 1:
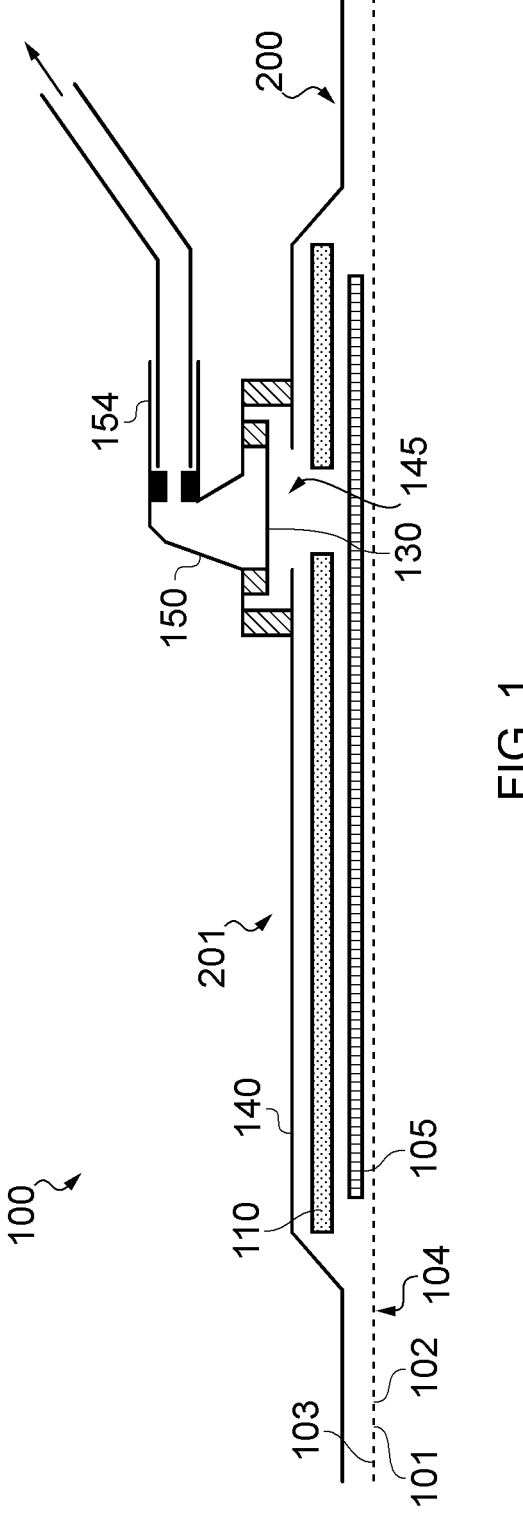
FIG. 1 illustrates an embodiment of a wound dressing system.

DETAILED DESCRIPTION OF THE
PREFERRED EMBODIMENT

Several modalities have been devised to quantify scars whether resulting from normal or aberrant wound healing or associated with fibrotic disorders. Scar assessments can be objective or subjective. Objective assessments provide a quantitative measurement of the scar whereas subjective assessments are observer-dependent. Certain embodiments of the present invention provide a method and apparatus for treating tissue whereby scar formation is inhibited, that is to say totally or partially prevented or reduced or whereby already formed scars can be reduced.

Additional applications disclosing wound dressing and wound treatment systems may be found in the following issued and co-pending patent applications: U.S. Pat. No. 7,964,766, issued Jun. 21, 2011 and titled "WOUND CLEANSING APPARATUS IN-SITU"; U.S. patent application Ser. No. 12/744,055 (published as US 2011/0172615), filed May 20, 2010 and titled "VACUUM ASSISTED WOUND DRESSING"; U.S. patent application Ser. No. 12/744,277 (published as US 2011/0028918), filed Sep. 20, 2010 and titled "WOUND DRESSING"; U.S. patent application Ser. No. 12/744,218 (published as US 2011/0054421), filed Sep. 20, 2010 and titled "WOUND DRESSING"; U.S. patent application Ser. No. 13/092,042, filed Apr. 21, 2011 and titled "WOUND DRESSING AND METHOD OF USE"; U.S. and PCT applications titled "SYSTEMS AND METHODS FOR CONTROLLING OPERATION OF A REDUCED PRESSURE THERAPY SYSTEM" and filed on Nov. 2, 2011; and U.S. and PCT applications titled "REDUCED PRESSURE THERAPY APPARATUSES AND METHODS OF USING SAME" and filed on Nov. 2, 2011. The entirety of these disclosures are hereby incorporated by reference.

Existing devices assess parameters associated with the scar such as pliability, firmness, colour, perfusion, thickness and 3-D topography. In this respect it is to be noted that there are currently at least five scar scales which have been designed to assess subjective parameters in an objective way. For example, the Vancouver Scar Scale (VSS), Manchester Scar Scale (MSS), Patient and Observer Scar Assessment Scale (POSAS), Visual Analogue Scale (VAS) and Stony Brook Scar Evaluation Scale (SBSES). More specifically, the VSS assesses parameters such as vascularity, height or thickness, pliability, and pigmentation of the scar. The VAS assesses parameters such as vascularity, pigmentation, acceptability, observer comfort, and the contours of the scar. The MSS assesses parameters including those from the VAS, as well as color, skin texture, relationship to surrounding skin, texture, margins, size, and number of scars. The POSAS assesses parameters including those from the VSS, as well as surface area, patient assessments of pain, itching, color, stiffness, thickness, and relief. The SBSES assesses parameters such as those from the VAS, as well as width, height, color, and the presence of suture or staple marks.

Certain embodiments of the present invention enable scar reduction or scar inhibition to occur relative to conventional treatment mechanisms and such reduction or inhibition can be observed according to one or more of the above-mentioned measuring techniques. Although the appearance of scars can be subjective to some extent, scars treated using embodiments described herein were observed to minimize scarring using the criteria set forth above. For example, treatment with the embodiments described herein caused a reduction in redness of the scar (such that the scar color more closely resembles that of the surrounding skin), a reduction in the height of the scar, reduced pruritus on and around the scar, and scar texture that more closely resembled that of the surrounding skin, as compared to traditional dressing methods.

Traditional dressing methods may include wound dressings with an absorbent pad and an adhesive-coated film or fibrous woven material layer, but without any additional negative pressure therapy. Such dressings include OPSITE POST OP® and PRIMAPORE®, manufactured by Smith & Nephew. The OPSITE POST OP® dressing comprises a high moisture vapor transmission rate polyurethane film top layer coated with an acrylic adhesive, an absorbent pad, and a low-adherency wound contact layer made from a perforated polyester film. The moisture vapor transmission rate of the top layer has a minimum value of 11000 g/m²/24 hrs at 37° C. in the presence of moisture. The PRIMAPORE® dressing comprises a non-woven viscose and polyester absorbent pad with a soft acrylic adhesive fixative layer.

Embodiments of the wound dressing system described herein applied to an incision were found to cause a significant reduction in scoring as compared to treatment with traditional dressing methods. For example, in one clinical trial, scars treated with an embodiment of the wound dressing disclosed herein showed a one-point improvement in both scar height and color in the VSS as compared to traditional OPSITE POST OP® dressings. Preferably, treatment with embodiments described herein cause a reduction of at least three points on the VSS or MSS compared to traditional dressing methods. Preferably statistically significant ($p<0.05$) reduction in scoring in the VSS or MSS of one point or more.

Figure 2:
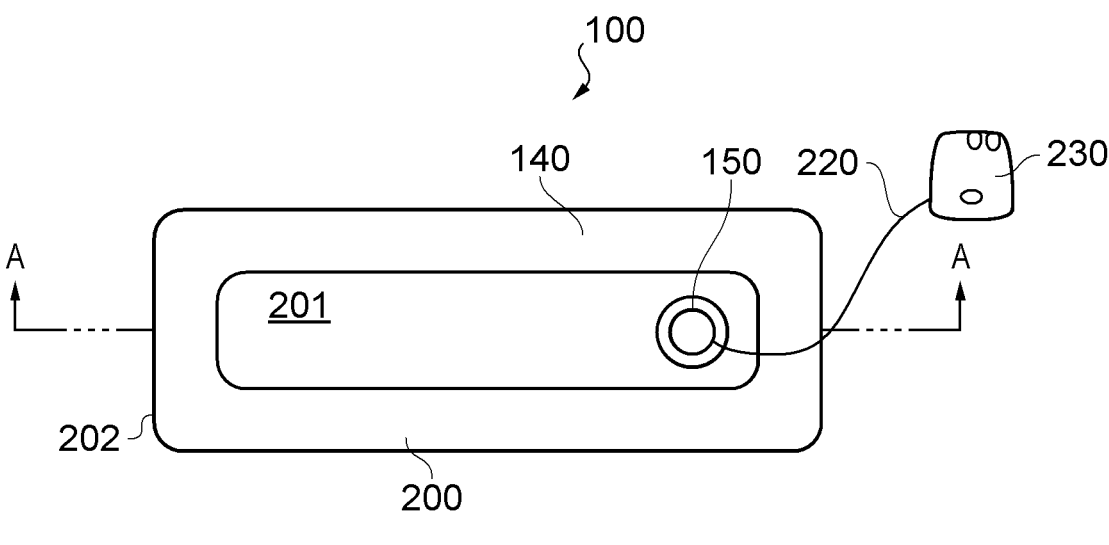
FIG. 2 illustrates an embodiment of a wound dressing system.

FIG. 1 illustrates a cross section through an embodiment of a wound dressing 100. A plan view from above the wound dressing 100 is illustrated in FIG. 2 with the line A-A indicating the location of the cross section shown in FIG. 1. It will be understood that FIG. 1 illustrates a generalised schematic view of an apparatus 100. It will be understood that embodiments of the present invention are generally applicable to use in topical negative pressure (TNP) therapy systems. Briefly, negative pressure therapy can assist in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilise the tissue in the apposed position of closure. A further beneficial use of TNP therapy can be found in grafts and flaps where removal of excess fluid is important and close proximity of the graft to tissue is required in order to ensure tissue viability.

The wound dressing 100 can be located over a wound site to be treated. The dressing 100 forms a sealed cavity over the wound site. It will be appreciated that throughout this specification reference is often made to a wound. In this sense it is to be understood that the term wound is to be broadly construed and encompasses open and closed wounds in which skin is torn, cut or punctured or where trauma causes a contusion. A wound is thus broadly defined as any damaged region of tissue where fluid may or may not be produced. Examples of such wounds include, but are not limited to, incisions, lacerations, abrasions, contusions, burns, diabetic ulcers, pressure ulcers, stoma, surgical wounds, trauma and venous ulcers or the like. Certain embodiments of the present invention are not restricted to use with wounds as will be discussed in more detail hereinbelow.

It is envisaged that the negative pressure range for certain embodiments of the present invention may be between about −20 mmHg and −200 mmHg (note that these pressures are relative to normal ambient atmospheric pressure thus, −200 mmHg would be about 560 mmHg in practical terms). Aptly the pressure range may be between about −40 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

It will be appreciated that according to certain embodiments of the present invention the pressure provided may be modulated over a period of time according to one or more desired and predefined pressure profiles. For example such a profile may include modulating the negative pressure between two predetermined negative pressures P1 and P2 such that pressure is held substantially constant at P1 for a pre-determined time period T1 and then adjusted by suitable means such as varying pump work or restricting fluid flow or the like, to a new predetermined pressure P2 where the pressure may be held substantially constant for a further predetermined time period T2. Two, three or four or more predetermined pressure values and respective time periods may be optionally utilised. Aptly more complex amplitude/ frequency wave forms of pressure flow profiles may also be provided eg sinusoidal, sore tooth, systolic-diastolic or the like etc.

As illustrated in FIG. 1 a lower surface 101 of the wound dressing 100 is provided by an optional wound contact layer 102. The wound contact layer 102 can be a polyurethane layer or polyethylene layer or other flexible layer which is perforated, for example via a hot pin process, laser ablation process, ultrasound process or in some other way or otherwise made permeable to liquid and gas. The wound contact layer has a lower surface 101 and an upper surface 103. The perforations 104 are through holes in the wound contact layer which enables fluid to flow through the layer. The wound contact layer helps prevent tissue ingrowth into the other material of the wound dressing. The perforations, when present, are small enough to meet this requirement but still allow fluid through. The wound contact layer helps hold the whole wound dressing together and helps to create an air tight seal around the absorbent pad in order to maintain negative pressure at the wound. The wound contact layer may also act as a carrier for an optional lower and upper adhesive layer (not shown). For example, a lower pressure sensitive adhesive may be provided on the underside surface 101 of the wound dressing whilst an upper pressure sensitive adhesive layer may be provided on the upper surface 103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilised this helps adhere the wound dressing to the skin around a wound site. Small perforations may also be made in the optional upper and lower adhesive layers.

Aptly, polysiloxanes or polyorganosiloxanes are the general category of polymer used to form the pressure sensitive silicone adhesive. For example, polydimethylsiloxane or the like can be used. Aptly, a formulation may be a mixture of alkyl pendant siloxanes and these are allowed to be spread and cast as a two part mix with a catalyst such that a final polymerisation step takes place following casting or spreading.

The moisture vapour permeability of the silicone layer (in a non-perforated form) has been tested with testing performed on a layer constructed as a non-perforated silicone adhesive (coat weight 130 grams per square meter (gsm) nominal) and full spread acrylic adhesive (27 to 37 gsm) coated onto opposite sides of an extruded EU30 polyurethane clear film (27 to 37 gsm). Moisture vapour permeability with the silicone layer in a lower position i.e. closest to the water in a Paddington cup has been measured. This helps mimic the direction of permeability when the product is used in a clinical setting. Results are shown below:

| Sample | Moisture Vapour Permeability $(gm^{-2}/24\ hrs)$ | | |
|---|---|---|---|
| Description | Results | | Mean |
| Non perforated silicone wound contact layer | 373 | 405    367 | 382 |

Aptly, the layer in the dressing which controls moisture vapour transmission rate (the silicone layer described in this specification is a suitable example of such a layer) has a moisture vapour permeability measured in gm-2/24 hrs of between 350 and 410. Aptly, the average moisture vapour permeability is around 380 gm-2/24 hrs. It will be appreciated that those skilled in the art may well consider a figure of less than 500 gm-2/24 hrs to amount to an impermeable layer. It will be appreciated that according to certain embodiments of the present invention a layer having a moisture vapour permeability in the range noted above can be provided at any suitable location in the wound dressing so as to control moisture vapour permeability and thus the environment of the tissue site. Aptly, this layer can be provided by a silicone adhesive wound contact layer.

An example of a suitable pressure sensitive adhesive is a Wacker silres PSA 45 adhesive. According to certain embodiments of the present invention a non-adhesive silicone layer may be used such as a Dow Corning 7-4107 elastomeric membrane. It will be understood that certain embodiments of the present invention are not restricted to the specific materials described for the silicone layer.

A layer 105 of porous material may be located above the wound contact layer. This porous layer behaves as a transmission layer which allows transmission of fluid including liquid and gas away from a wound site into upper layers of the wound dressing. In particular, the transmission layer 105 ensures that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalised negative pressure. The layer 105 is formed of a material having a three dimensional structure. For example, a knitted or woven spacer fabric (for example Baltex 7970 weft knitted polyester). Other materials could of course be utilised.

Aptly, the transmission layer comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 100 denier flat polyester and a third layer formed sandwiched between these two layers which is a region defined by a knitted polyester viscose, cellulose or the like monofilament fibre. Other materials and other linear mass densities of fibre could of course be used.

Whilst reference is made throughout this disclosure to a monofilament fibre it will be appreciated that a multistrand alternative could of course be utilised.

The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Aptly, to improve the liquid flow across the transmission layer (that is to say perpendicular to the channel region formed between the top and bottom spacer layers, the 3D fabric is treated with a dry cleaning agent (such as, but not limited to, perchloro ethylene) to help remove any manufacturing products such as mineral oils, fats and/or waxes used previously which might interfere with the hydrophilic capabilities of the transmission layer. Aptly, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 110 of absorbent material may be provided above the transmission layer 105. The absorbent material which may be a foam or non-woven natural or synthetic material and which may optionally include or be super-absorbent material forms a reservoir for fluid, particularly liquid, removed from the wound site and draws those fluids towards a cover layer 140. The material of the absorbent layer also prevents liquid collected in the wound dressing from flowing in a sloshing manner. The absorbent layer 110 also helps distribute fluid throughout the layer via a wicking action so that fluid is drawn from the wound site and stored throughout the absorbent layer. This helps prevent agglomeration in areas of the absorbent layer. The capacity of the absorbent material should preferably be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 110 may typically be manufactured from ALLEVYN™ foam, Freudenberg 114-224-4 and/or Chem-Posite™11C-450.

Aptly, the absorbent layer is a layer of non-woven cellulose fibres having super-absorbent material in the form of dry particles dispersed throughout. Use of the cellulose fibres introduces fast wicking elements which help quickly and evenly distribute liquid taken up by the dressing. The juxtaposition of multiple strand-like fibres leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing.

The wicking action also assists in delivering liquid downwards towards the wound bed when exudation slows or halts. This delivery process helps maintain the transmission layer and lower wound bed region in a moist state which helps prevent crusting within the dressing (which could lead to blockage) and helps maintain an environment optimised for wound healing.

Aptly, the absorbent layer may be an air-laid material. Heat fusible fibres may optionally be used to assist in holding the structure of the pad together. It will be appreciated that rather than using super-absorbing particles or in addition to such use, super-absorbing fibres may be utilised according to certain embodiments of the present invention. An example of a suitable material is the Product Chem-Posite™ 11 C available from Emerging Technologies Inc (ETi) in the USA.

Optionally, according to certain embodiments of the present invention, the absorbent layer may include synthetic stable fibres and/or bi-component stable fibres and/or natural stable fibres and/or super-absorbent fibres. Fibres in the absorbent layer may be secured together by latex bonding or thermal bonding or hydrogen bonding or a combination of any bonding technique or other securing mechanism. Aptly, the absorbent layer is formed by fibres which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer preferably comprises a layer of multiple fibres. Aptly, the fibres are strand-like and made from cellulose, polyester, viscose or the like. Aptly, dry absorbent particles are distributed throughout the absorbent layer ready for use. Aptly, the absorbent layer comprises a pad of cellulose fibres and a plurality of super absorbent particles. Aptly, the absorbent layer is a non-woven layer of randomly orientated cellulose fibres.

Super-absorber particles/fibres may be, for example, sodium polyacrylate or carbomethoxycellulose materials or the like or any material capable of absorbing many times its own weight in liquid. Aptly, the material can absorb more than five times its own weight of 0.9% W/W saline, etc. Aptly, the material can absorb more than 15 times its own weight of 0.9% W/W saline, etc. Aptly, the material is capable of absorbing more than 20 times its own weight of 0.9% W/W saline, etc. Aptly, the material is capable of absorbing more than 30 times its own weight of 0.9% W/W saline, etc.

Aptly, the particles of superabsorber are very hydrophilic and grab the fluid as it enters the dressing, swelling up on contact. An equilibrium is set up within the dressing core whereby moisture passes from the superabsorber into the dryer surrounding area and as it hits the top film the film switches and the fluid vapour starts to be transpired. A moisture gradient is established within the dressing to continually remove fluid from the wound bed and ensure the dressing does not become heavy with exudate.

Aptly the absorbent layer includes at least one through hole located so as to underly the suction port. As illustrated in FIG. 1 a single through hole can be used to produce an opening underlying the port 150. It will be appreciated that multiple openings could alternatively be utilised. Additionally should more than one port be utilised according to certain embodiments of the present invention one or multiple openings may be made in the super-absorbent layer in registration with each respective port. Although not essential to certain embodiments of the present invention the use of through holes in the super-absorbent layer provide a fluid flow pathway which is particularly unhindered and this is useful in certain circumstances.

Where an opening is provided in the absorbent layer the thickness of the layer itself will act as a stand-off separating any overlying layer from the upper surface (that is to say the surface facing away from a wound in use) of the transmission layer 105. An advantage of this is that the filter of the port is thus decoupled from the material of the transmission layer. This helps reduce the likelihood that the filter will be wetted out and thus will occlude and block further operation.

Use of one or more through holes in the absorption layer also has the advantage that during use if the absorbent layer contains a gel forming material, such as superabsorber, that material as it expands to absorb liquid, does not form a barrier through which further liquid movement and fluid movement in general cannot pass. In this way each opening in the absorbent layer provides a fluid pathway between the transmission layer directly to the wound facing surface of the filter and then onwards into the interior of the port.

A gas impermeable, but moisture vapour permeable, cover layer 140 preferably extends across the width of the wound dressing. The cover layer, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer 140 is sealed to the wound contact layer 102 in a border region 200 around the circumference of the dressing, ensuring that no air is drawn in through the border area, for example via adhesive or welding techniques. The cover layer 140 protects the wound from external bacterial contamination (bacterial barrier) and allows liquid from wound exudates to be transferred through the layer and evaporated from the film outer surface. The cover layer 140 typically comprises two layers; a polyurethane film and an adhesive pattern spread onto the film. The polyurethane film is moisture vapour permeable and may be manufactured from a material that has an increased water transmission rate when wet.

The absorbent layer 110 may be of a greater area than the transmission layer 105, such that the absorbent layer overlaps the edges of the transmission layer 105, thereby ensuring that the transmission layer does not contact the cover layer 140. This provides an outer channel 115 of the absorbent layer 110 that is in direct contact with the wound contact layer 102, which aids more rapid absorption of exudates to the absorbent layer. Furthermore, this outer channel 115 ensures that no liquid is able to pool around the circumference of the wound cavity, which may otherwise seep through the seal around the perimeter of the dressing leading to the formation of leaks.

In order to ensure that the air channel remains open when a vacuum is applied to the wound cavity, the transmission layer 105 is preferably sufficiently strong and non-compliant to resist the force due to the pressure differential. However, if this layer comes into contact with the relatively delicate cover layer 140, it can cause the formation of pin-hole openings in the cover layer 140 which allow air to leak into the wound cavity. This may be a particular problem when a switchable type polyurethane film is used that becomes weaker when wet. The absorbent layer 110 is generally formed of a relatively soft, non-abrasive material compared to the material of the transmission layer 105 and therefore does not cause the formation of pin-hole openings in the cover layer. Thus by providing an absorbent layer 110 that is of greater area than the transmission layer 105 and that overlaps the edges of the transmission layer 105, contact between the transmission layer and the cover layer is prevented, avoiding the formation of pin-hole openings in the cover layer 140.

The absorbent layer 110 is positioned in fluid contact with the cover layer 140. As the absorbent layer absorbs wound exudate, the exudate is drawn towards the cover layer 140, bringing the water component of the exudate into contact with the moisture vapour permeable cover layer. This water component is drawn into the cover layer itself and then evaporates from the top surface of the dressing. In this way, the water content of the wound exudate can be transpired from the dressing, reducing the volume of the remaining wound exudate that is to be absorbed by the absorbent layer 110, and increasing the time before the dressing becomes full and should be changed. This process of transpiration occurs even when negative pressure has been applied to the wound cavity, and it has been found that the pressure difference across the cover layer when a negative pressure is applied to the wound cavity has negligible impact on the moisture vapour transmission rate across the cover layer.

An orifice 145 is provided in the cover film 140 to allow a negative pressure to be applied to the dressing 100. A suction port 150 is sealed to the top of the cover film 140 over the orifice 145, and communicates negative pressure through the orifice 145. A length of tubing 220 may be coupled at a first end to the suction port 150 and at a second end to a pump unit (not shown) to allow fluids to be pumped out of the dressing. The port may be adhered and sealed to the cover film 140 using an adhesive such as an acrylic, cyanoacrylate, epoxy, UV curable or hot melt adhesive. The port 150 is formed from a soft polymer, for example a polyethylene, a polyvinyl chloride, a silicone, or polyurethane having a hardness of 30 to 90 on the Shore A scale.

An aperture is provided in the absorbent layer 110 beneath the orifice 145 such that the orifice is connected directly to the transmission layer 105. This allows the negative pressure applied to the port 150 to be communicated to the transmission layer 105 without passing through the absorbent layer 110. This ensures that the negative pressure applied to the wound site is not inhibited by the absorbent layer as it absorbs wound exudates. In other embodiments, no aperture may be provided in the absorbent layer 110, or alternatively a plurality of apertures underlying the orifice 145 may be provided.

A filter element 130 that is impermeable to liquids, but permeable to gasses is provided to act as a liquid barrier, and to ensure that no liquids are able to escape from the wound dressing. The filter element may also function as a bacterial barrier. Typically the pore size is 0.2 $\mu$m. Suitable materials for the filter material of the filter element 130 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film 140 over the orifice 145. For example, the filter element 130 may be moulded into the port 150, or may be adhered to both the top of the cover layer 140 and bottom of the port 150 using an adhesive such as, but not limited to, a UV cured adhesive.

It will be understood that other types of material could be used for the filter element 130. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 130 comprises a support layer and an acrylic co-polymer membrane formed on the support layer. Aptly the wound dressing 100 according to certain embodiments of the present invention uses microporous hydrophobic membranes (MHMs). Numerous polymers may be employed to form MHMs. For example, PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 130 may also include an odour absorbent material, for example activated charcoal, carbon fibre cloth or Vitec Carbotec® Q2003073 foam, or the like. For example, an odour absorbent material may form a layer of the filter element 130 or may be sandwiched between microporous hydrophobic membranes within the filter element.

The filter element 130 thus enables gas to be exhausted through the orifice 145. Liquid, particulates and pathogens however are contained in the dressing.

In operation the wound dressing 100 is sealed over a wound site forming a wound cavity. A pump unit (not shown) applies a negative pressure at a connection portion 154 of the port 150 which is communicated through the orifice 145 to the transmission layer 105. Fluid is drawn towards the orifice through the wound dressing from a wound site below the wound contact layer 102. The fluid moves towards the orifice through the transmission layer 105. As the fluid is drawn through the transmission layer 105 wound exudate is absorbed into the absorbent layer 110.

Turning to FIG. 2 which illustrates a wound dressing 100 in accordance with an embodiment of the present invention one can see the upper surface of the cover layer 140 which extends outwardly away from a centre of the dressing into a border region 200 surrounding a central raised region 201 overlying the transmission layer 105 and the absorbent layer 110. As indicated in FIG. 2 the general shape of the wound dressing is rectangular with rounded corner regions 202. It will be appreciated that wound dressings according to other embodiments of the present invention can be shaped differently such as square, circular or elliptical dressings, or the like.

When a negative pressure is applied to the port 150 from a pump 230 via conduit 220, the negative pressure is communicated to the wound cavity below the cover layer. This negative pressure is thus experienced at the target wound site. Fluid including air and wound exudate is drawn through the wound contact layer and transmission layer 105. The wound exudate drawn through the lower layers of the wound dressing is dissipated and absorbed into the absorbent layer 110 where it is collected and stored. Air and moisture vapour is drawn upwards through the wound dressing through the filter layer and out of the dressing through the suction port. A portion of the water content of the wound exudate is drawn through the absorbent layer and into the cover layer 140 and then evaporates from the surface of the dressing.

Figure 3:
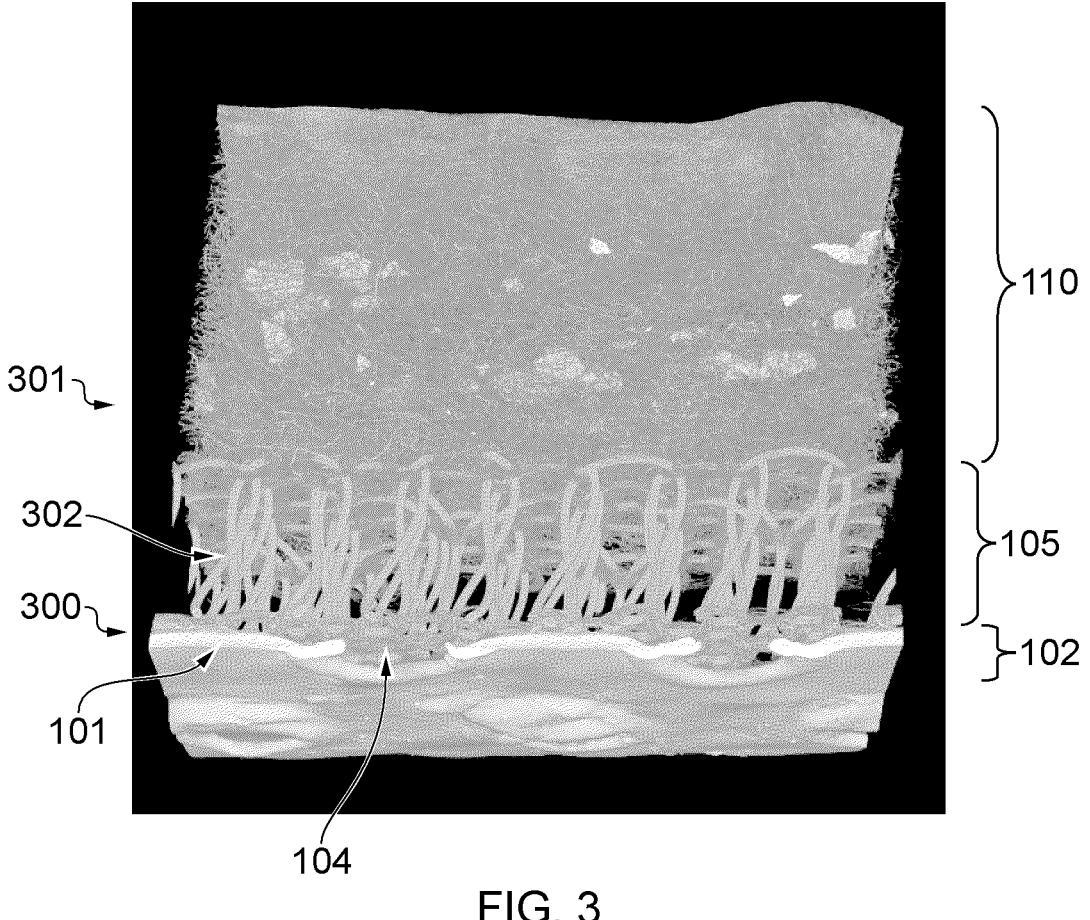
FIG. 3 illustrates layers in an embodiment of a wound dressing system.

FIG. 3 illustrates a cross-section of a portion of the dressing shown in FIGS. 1 and 2. In particular, FIG. 3 illustrates a magnified view of the wound contact layer 102 which includes a lower surface 101 and multiple perforations 104 formed as through holes. An upper surface 104 of the wound contact layer abuts a first layer 300 of the transmission layer 105. A further, upper, layer 301 of the transmission layer 105 is spaced apart from the first layer. The first and further layers of the transmission layer are kept apart in a spaced apart relationship by multiple monofilament fibre spacers 302 which act as resilient flexible pillars separating the two layers of the transmission layer. The upper layer 301 of the transmission layer is adjacent a lower surface of the absorbent 110 which, for example, is formed as a pad of fibrous cellulose material interspaced with super-absorbent particulate matter.

The absorbent layer 110 holds liquid collected during the application of negative pressure therapy. By having this layer in fluid communication with, and preferably in contact with, the layer of the transmission layer, the region of the transmission layer 105 is kept at a moist environment. This helps avoid build-up and crusting of the exudate during use.

Figure 4:
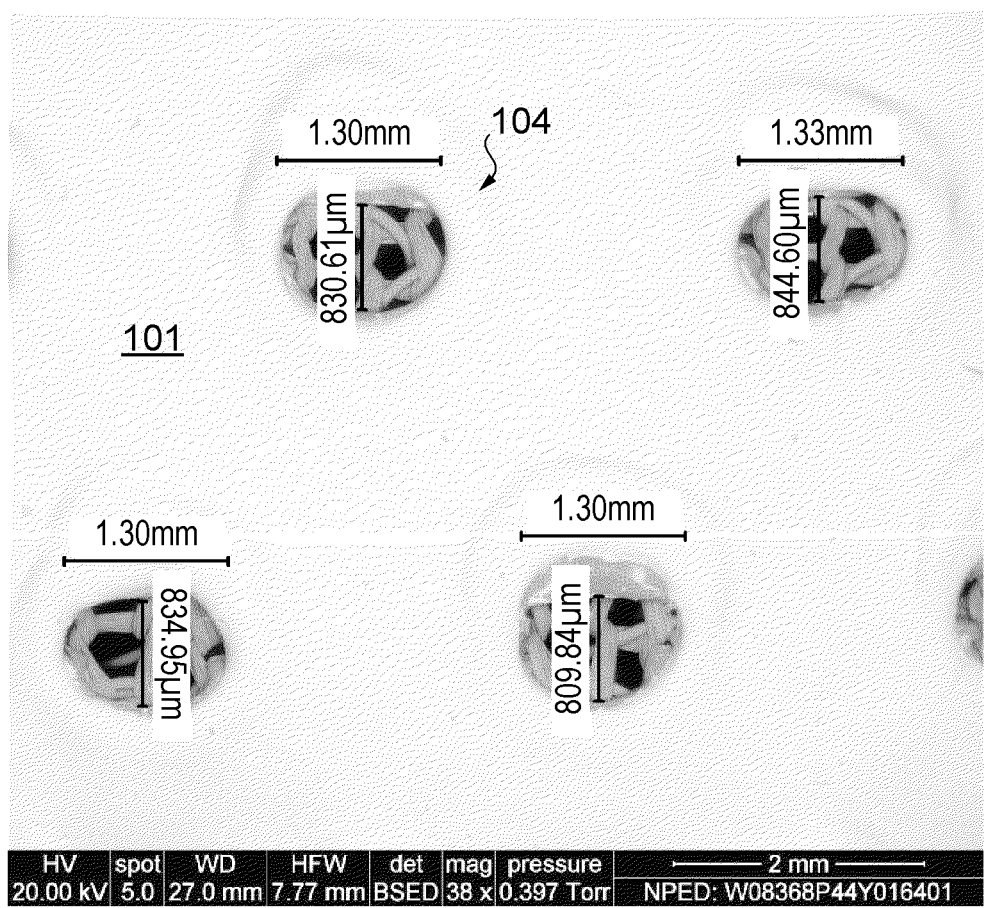
FIG. 4 illustrates an open area of openings in an embodiment of a wound contact layer.

FIG. 4 illustrates a view of an underside of the wound dressing. More particularly, a lower surface 101 of the wound dressing 100 is part of a wound contact layer 102. Aptly, the wound contact layer 102 is a polyurethane layer or polyethylene layer or other flexible layer which is perforated. Aptly, materials are selected from the Triboelectric series of materials which become negative in charge when brought into contact with other materials. Such materials can be, but are not limited to, polyester, polyurethane, saran wrap, polyethylene, polypropylene, silicone film and/or vinyl (pvc) or the like. As illustrated in FIG. 4, the perforations 104 are through holes in the wound contact layer. The perforations may be formed as slits or slots or substantially circular holes. Aptly, the circular holes have a size ranging from 0.025 mm to 1.5 mm. The opening of each perforation has a cross-sectional area which is referred to as an open area. The open area provided by the openings when related to the total area presented by the underside of the dressing is sufficiently small so as to help prevent tissue ingrowth into the wound dressing, allowing wound exudate to flow into the dressing, and to maintain a level of hydration below the dressing and provide access of oxygen to the surface of the underlying skin in use whereby scar formation is prevented or reduced. Aptly, the open area of openings is around 20% or less of a total area. Aptly, the open area is around 17.5% or less of a total area. The open area is large enough to enable full communication of negative pressure to the underlying tissue. That is to say there is little or no pressure difference on either side of the layer.

As illustrated in FIG. 4, each opening 104 in the wound contact layer 101 is a through hole and reveals a respective region of the transmission layer lying within the dressing on a side of the wound contact layer distal from the wound/tissue in use. Aptly, the transmission layer material is selected from a material in the Triboelectric series which becomes negative in charge and will thus tend to attract electrons when brought into contact with other materials.

In use, location of a wound dressing having a silicone adhesive wound contact layer may help restore a barrier function of the stratum corneum of an underlying wound. This helps reduce or minimise transepidermal water loss (TEWL) which would otherwise occur. By helping to reduce TEWL stimulation of the various stages in a normal healing process, which would lead to excessive collagen production and abnormal scarring, may be prevented wholly or partially. Provision of a limited open area in the wound contact layer may enable such TEWL to be controlled so as to assist in an anti-scarring and yet may also enable negative pressure therapy to be applied to the underlying tissue.

This contemporaneous application of negative pressure therapy may help apply pressure simultaneously to the tissue. This may assist in reducing scar formation. Negative pressure application may also help contract and/or compress the whole underlying tissue. Compression may also help prevent upward overgrowth of tissue. This may in turn help to reduce the raised appearance of a scar. Contraction may help with a position of the epidermis of an underlying wound region. This may thus reduce the need for excess tissue growth which might otherwise lead to scar tissue formation.

Aptly, the simultaneous application of NPT also increases build-up of electrostatic charge between the dressing and tissue. The interaction between negatively charged ions of the dressing and ionic charges of the tissue may help contribute to wound and scar healing.

Aptly, having a silicone adhesive as a wound contacting surface layer enables the topical application of silicone oils which may leak from the adhesive layer. Aptly, cotemporaneous application of compression forces adhesive forces and a dressing which helps buffer external shear forces means that a particularly optimum environment is provided to assist in scar free healing/tissue formation. This may lead to improved inhibition of scar formation.

Figure 5:
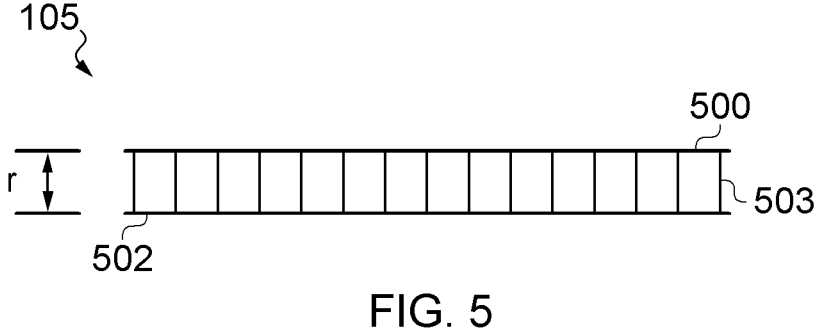
FIG. 5 illustrates an embodiment of a transmission layer in a relaxed mode of operation.

FIG. 5 illustrates a first, upper surface 500 and a further, lower surface 502 of a transmission layer 105 according to an embodiment of the present invention. In the embodiment illustrated in FIG. 5 fibres 503 of a woven layer extend between the first surface 500 and the further surface 502. It will be appreciated that according to further embodiments of the present invention if a foam layer is used as a transmission layer 105 the connected strands forming the foam will act as spacer elements. As illustrated in FIG. 5 in a relaxed mode of operation, that is to say when in use, no negative pressure is applied to the wound dressing or negative pressure is applied to the wound dressing but no external force acts on the wound dressing then the fibres 503 extend substantially perpendicular to the upper and lower surfaces keeping the surfaces in a spaced apart substantially parallel configuration.

Figure 6:
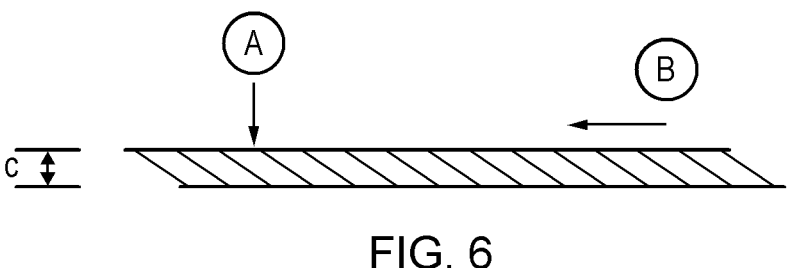
FIG. 6 illustrates an embodiment of a transmission layer in a forced mode of operation.

FIG. 6 illustrates the transmission layer 105 when an external force is exerted on the outside of the dressing. The external force can be a compressive force indicated by arrow A and/or a lateral force illustrated by arrow B in FIG. 6. As indicated either a compressive force or a lateral force acts to cause the fibres 503 to lean to one side. This causes the upper and lower surfaces to become laterally offset with respect to each other as well as causing the thickness of the layer to reduce from a separation distance r indicated in FIG. 5 in a relaxed mode of operation to a compression distance c illustrated in FIG. 6. The reduction in thickness effectively provides some "give" in the dressing even when the dressing is subject to negative pressure. It will be appreciated that the forces acting on the dressing may occur throughout the whole of the surface area of the dressing or only in one or more particular regions. In such a situation regions of the dressing can be in a relaxed mode of operation and further regions can be in a compressed mode of operation. As illustrated in FIG. 6 when a force is exerted on the transmission layer the fibres separating the upper and lower surfaces tend to lean to one side sharing a common lean angle.

Throughout this specification reference will be made to a relaxed mode of operation and a forced mode of operation. It is to be understood that the relaxed mode of operation corresponds to a natural state of the material either when no negative pressure is applied or when negative pressure is applied. In either situation no external force, caused for example by motion of a patient or an impact is in evidence. By contrast a forced mode of operation occurs when an external force whether compressive, lateral or other is brought to bear upon the wound dressing. Such forces can cause serious damage/prevent healing or a wound.

Figure 7:
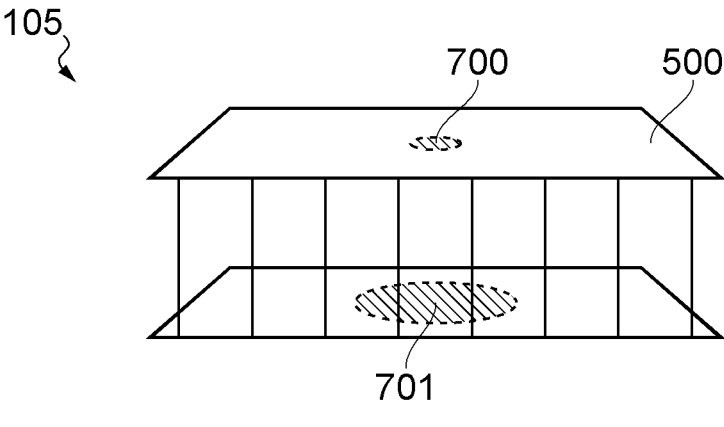
FIG. 7 illustrates pressure offsetting.

FIG. 7 illustrates how certain embodiments of the present invention can also operate to offset load forces. As illustrated in FIG. 7 if a force is exerted over a contact area 700 in an upper surface 500 of the transmission layer 105 then this force is transmitted across and through the transmission layer and is exerted over a larger dissipation area 701 against an underlying wound site. In the case of use of a 3D knit as a transmission layer this is because the relatively stiff spacer elements provide at least some lateral stiffness to the layer.

Figure 8:
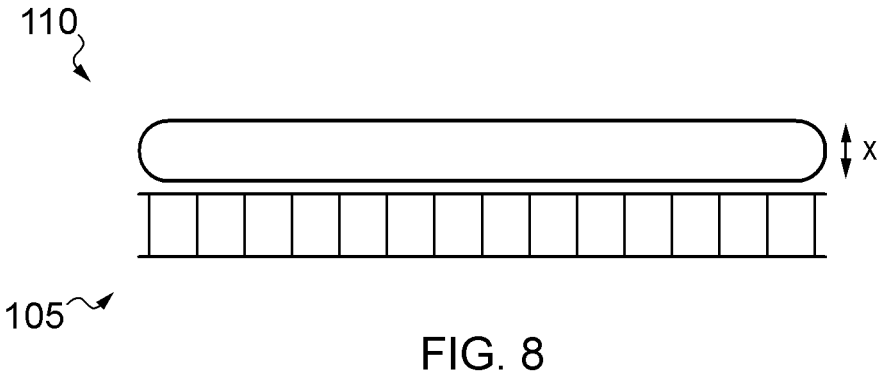
FIG. 8 illustrates an embodiment of a transmission layer and overlying absorbent in a relaxed mode of operation.
Figure 9:
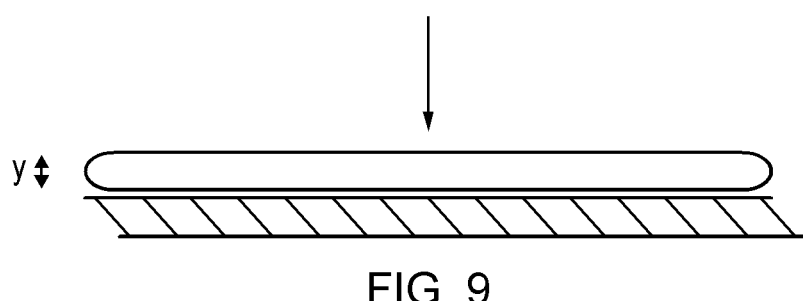
FIG. 9 illustrates an embodiment of an absorbent layer and transmission layer experiencing a compressive force.
Figure 10:
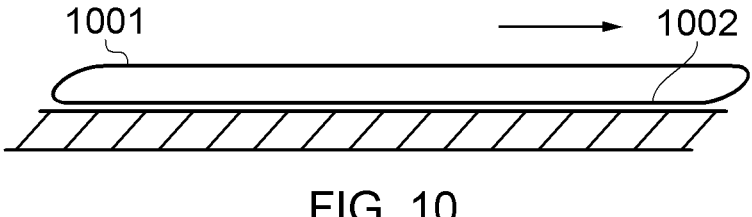
FIG. 10 illustrates an embodiment of an absorbent layer and transmission layer experiencing a sheet force.

FIG. 8 illustrates the transmission layer 105 and absorbent layer 110 in more detail. The absorbent layer 110 is located proximate to the upper surface 500 of the transmission layer 105 and is unbonded thereto according to certain embodiments of the present invention. When unbonded the absorbent layer 110 is also able to move laterally with respect to the underlying transmission layer when a lateral or shear force is applied to the wound dressing. Also the absorbent layer is able to further compress when a compressive force illustrated in FIG. 9 acts on the wound dressing. As illustrated in FIG. 9 the absorbent layer 110 decreases in thickness under a compressive force from a non-compressed thickness x illustrated in FIG. 8 to a compressed distance y illustrated in FIG. 9. The compressive force also acts to offset the upper and lower surfaces of the transmission layer as described above thus enhancing the "give" of the dressing. The ability for an upper surface 1001 to translate laterally with respect to a lower surface 1002 of the absorbent layer under a lateral or shearing force exerted on the wound dressing is illustrated in more detail in FIG. 10. This lateral motion causes the thickness x of the absorbent layer 110 to reduce and the upper surface and lower surface of the absorbent layer to be offset with respect to each other. This effect can itself be sufficient to prevent shear forces exerted on the whole or part of the wound dressing from being transferred to an underlying wound bed. As can the corresponding effect in the transmission layer. However a combination enhances the cushioning effect. If the wound bed comprises a skin graft region the reduction of shear forces can be particularly advantageous.

It is to be noted that in use the dressing may be used "up-side down", at an angle or vertical. References to upper and lower are thus used for explanation purposes only.

Figure 11:
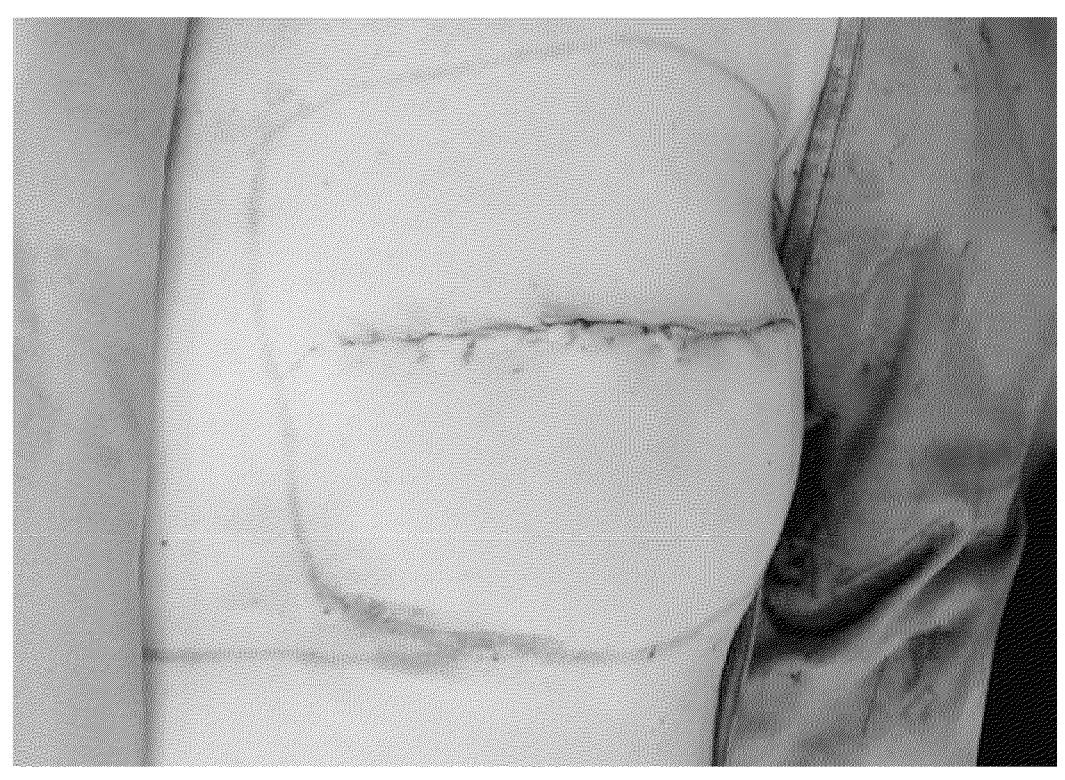
FIG. 11 illustrates a post surgical wound.

FIG. 11 illustrates results of application of NPWT to a 41 year old woman who had previously been receiving treatment for breast cancer. Following radiotherapy, the woman underwent surgery for a tissue expander to be placed into her breast for reconstruction. The post-surgical wound following this breast reconstruction is illustrated in FIG. 11. The wound measured 15 cm in length and 0.5 cm in width. It is to be noted that the closed incision is raised above the level of the surrounding skin.

Figure 12:
FIG. 12 illustrates the wound of FIG. 11 with an embodiment of a wound dressing system in place.

FIG. 12 illustrates application of a wound dressing with the dressing in place on the patient on a first assessment day (day 1). A dressing 30 cm by 10 cm was selected to deal with any exudates and apply NPWT to the incision line to minimise risk to the wound while also minimising inconvenience to the patient. Although not illustrated in FIG. 12 (but illustrated later in FIG. 13) a tunnelled IV site is situated beneath the patient's collarbone above the location of the dressing and this was covered with a conventional dressing.

Figure 13:
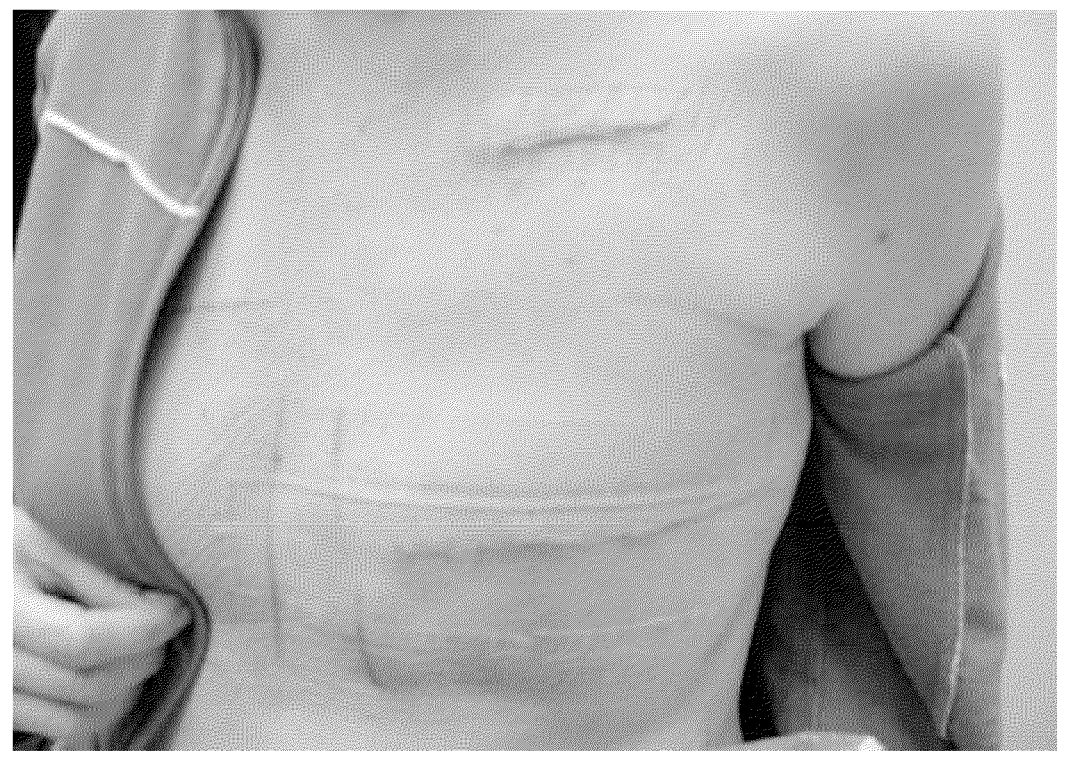
FIG. 13 illustrates a comparison with a wound treated with a conventional dressing and the embodiment of a dressing system shown in FIG. 12.

Following application of the dressing, the patient was allowed to go home with the dressing and pump and was seen daily as an outpatient from day 2. The pump was changed on day 6 and the dressing changed on day 11. FIG. 13 illustrates the post-surgical wound after dressing removal on day 11. Some indentation is shown from the dressing itself but otherwise healthy surrounding skin is evident. The surgical incision is closed and there is no exudate and the incision is flat. This may be compared with the tunnelled IV site wound of the same age but treated with a conventional dressing which remains raised, broader and redder.

Figure 14A:
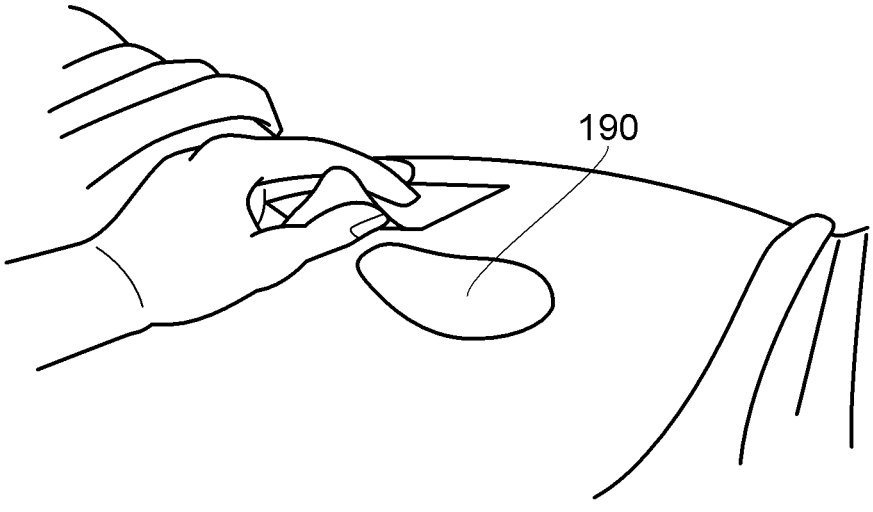
FIGS. 14A-D illustrate the use and application of an embodiment of a wound treatment system onto a patient.

FIGS. 14A-D illustrate the use of an embodiment of a TNP wound treatment system being used to treat a wound site on a patient. FIG. 14A shows a wound site 190 being cleaned and prepared for treatment. Here, the healthy skin surrounding the wound site 190 is preferably cleaned and excess hair removed or shaved. The wound site 190 may also be irrigated with sterile saline solution if necessary. Optionally, a skin protectant may be applied to the skin surrounding the wound site 190. If necessary, a wound packing material, such as foam or gauze, may be placed in the wound site 190. This may be preferable if the wound site 190 is a deeper wound.

Figure 14B:
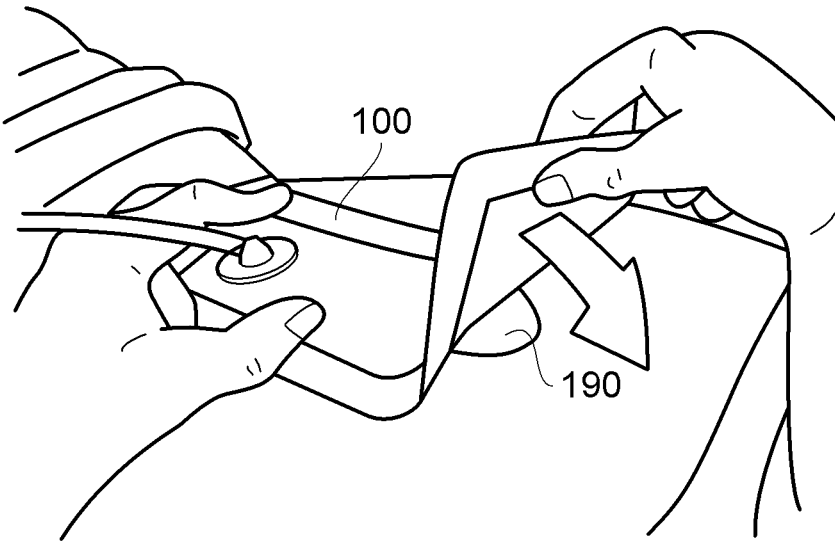

After the skin surrounding the wound site 190 is dry, and with reference now to FIG. 14B, the wound dressing 100 may be positioned and placed over the wound site 190. Preferably, the wound dressing 100 is placed with the wound contact layer 102 over and/or in contact with the wound site 190. In some embodiments, an adhesive layer is provided on the lower surface 101 of the wound contact layer 102, which may in some cases be protected by an optional release layer to be removed prior to placement of the wound dressing 100 over the wound site 190. Preferably, the dressing 100 is positioned such that the port 150 is in a raised position with respect to the remainder of the dressing 100 so as to avoid fluid pooling around the port. In some embodiments, the dressing 100 is positioned so that the port 150 is not directly overlying the wound, and is level with or at a higher point than the wound. To help ensure adequate sealing for TNP, the edges of the dressing 100 are preferably smoothed over to avoid creases or folds.

Figure 14C:
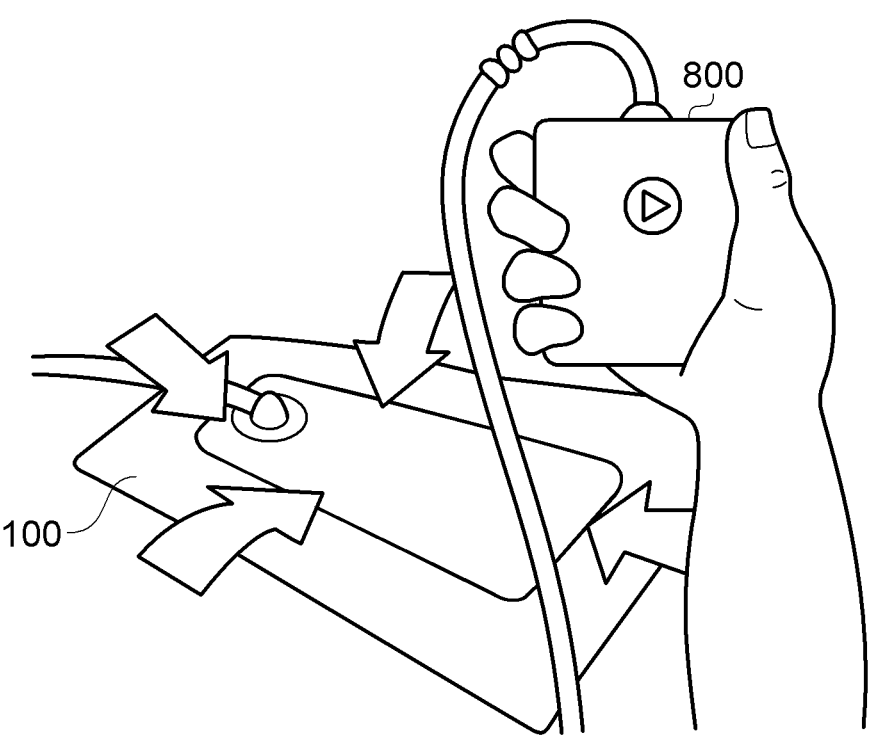

With reference now to FIG. 14C, the dressing 100 is connected to the pump 800. The pump 800 is configured to apply negative pressure to the wound site via the dressing 100, and typically through a conduit. In some embodiments, and as described above in FIG. 28, a connector may be used to join the conduit from the dressing 100 to the pump 800. Upon the application of negative pressure with the pump 800, the dressing 100 may in some embodiments partially collapse and present a wrinkled appearance as a result of the evacuation of some or all of the air underneath the dressing 100. In some embodiments, the pump 800 may be configured to detect if any leaks are present in the dressing 100, such as at the interface between the dressing 100 and the skin surrounding the wound site 190. Should a leak be found, such leak is preferably remedied prior to continuing treatment.

Figure 14D:
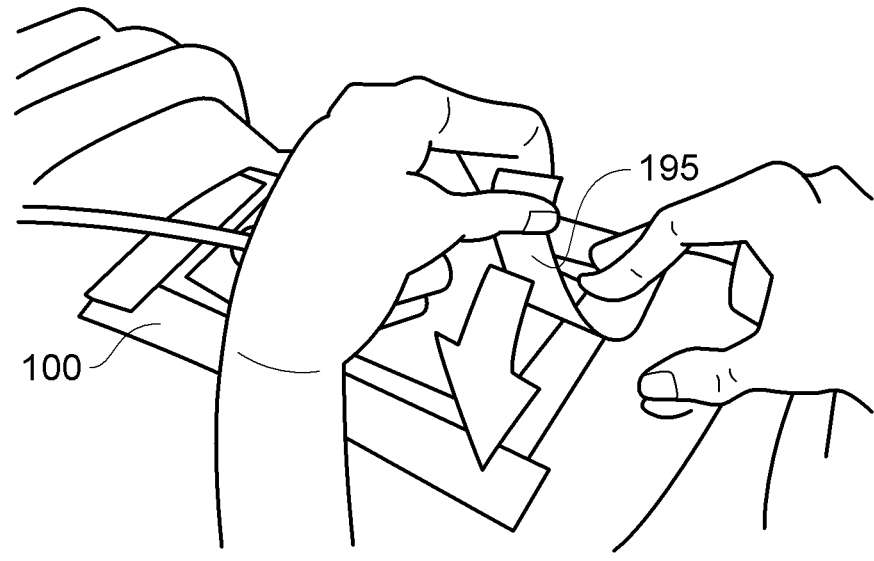

Turning to FIG. 14D, additional fixation strips 195 may also be attached around the edges of the dressing 100. Such fixation strips 195 may be advantageous in some situations so as to provide additional sealing against the skin of the patient surrounding the wound site 190. For example, the fixation strips 195 may provide additional sealing for when a patient is more mobile. In some cases, the fixation strips 195 may be used prior to activation of the pump 800, particularly if the dressing 100 is placed over a difficult to reach or contoured area.

Treatment of the wound site 190 preferably continues until the wound has reached a desired level of healing. In some embodiments, it may be desirable to replace the dressing 100 after a certain time period has elapsed, or if the dressing is full of wound fluids. During such changes, the pump 800 may be kept, with just the dressing 100 being changed.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. An apparatus for promoting scar-free healing at a tissue site, the apparatus comprising:
   a tissue contact layer comprising silicone and a plurality of perforations the combined open area of the perforations comprising around 20% or less of the total area of a single side of the tissue contact layer, the silicone in the tissue contact layer comprising a moisture vapor transmission rate of between about 350 to 410 $gm^{-2}/24$ hrs when unperforated;
   a source of negative pressure connectable to the tissue site and configured to apply negative pressure through the tissue contact layer to a wounded area beneath the tissue contact layer;
   wherein the tissue contact layer is configured to reduce transepidermal water loss after negative pressure is applied through the tissue contact layer for a period of time, compared to if the negative pressure is applied at the tissue site without using the tissue contact layer; and
   wherein the tissue contact layer is configured to reduce scar tissue formation by at least one point on the Vancouver or Manchester Scar Scale after negative pressure is applied through the tissue contact layer for a period of time sufficient to close the wound, compared to if negative pressure is applied at the tissue site without using said tissue contact layer.

2. The apparatus of claim 1, further comprising a transmission layer positioned over the tissue contact layer.

3. The apparatus of claim 2, further comprising an absorbent layer configured to absorb wound exudate, the absorbent layer positioned over the transmission layer.

4. The apparatus of claim 1, wherein the tissue contact layer comprises a basis weight of about 130 gsm when unperforated.

5. The apparatus of claim 1, wherein the tissue contact layer comprises a moisture vapor transmission rate of about 380 $gm^{-2}/24$ hrs when unperforated.

6. The apparatus of claim 1, further comprising a cover layer comprising a fluid passage.

7. The apparatus of claim 1, wherein the silicone comprises polysiloxane, polyorganosiloxane, or polydimethylsiloxane.

8. The apparatus of claim 1, wherein the combined area of the apertures comprises about 17.5% or less of the total area of a single side of the tissue contact layer.

9. An apparatus for promoting scar-free healing at a tissue site, the apparatus comprising:
   a tissue contact layer comprising silicone and a plurality of perforations, individual perforations comprising an average diameter of 0.025 mm to 1.5 mm, the combined open area of the perforations comprising around 20% or less of the total area of a single side of the tissue contact layer;

a source of negative pressure connectable to the tissue site and configured to apply negative pressure through the tissue contact layer to a wounded area beneath the tissue contact layer;

wherein the silicone comprises polysiloxane, polyorganosiloxane, or polydimethylsiloxane; and wherein the tissue contact layer is configured to reduce scar tissue formation by at least one point on the Vancouver or Manchester Scar Scale after negative pressure is applied through the tissue contact layer for a period of time sufficient to close the wound, compared to if negative pressure is applied at the tissue site without using said tissue contact layer.

10. The apparatus of claim 9, further comprising a transmission layer positioned over the tissue contact layer.

11. The apparatus of claim 10, further comprising an absorbent layer configured to absorb wound exudate, the absorbent layer positioned over the transmission layer.

12. The apparatus of claim 9, further comprising a cover layer comprising a fluid passage.

13. The apparatus of claim 9, wherein the combined area of the apertures comprises about 17.5% or less of the total area of a single side of the tissue contact layer.

14. An apparatus for promoting scar-free healing at a tissue site where negative pressure is applied, the apparatus comprising:

a tissue contact layer comprising silicone and a plurality of perforations, the combined open area of the perforations comprising about 20% or less of the total area of a single side of the tissue contact layer;

a source of negative pressure connectable to the tissue site and configured to apply negative pressure through the tissue contact layer to a wounded area beneath the tissue contact layer;

a transmission layer positioned over the tissue contact layer, the transmission layer configured to distribute negative pressure; and a cover layer positioned over the transmission layer, the cover layer comprising an opening, the opening configured to connect to the source of negative pressure; and wherein the tissue contact layer is configured to reduce scar tissue formation by at least one point on the Vancouver or Manchester Scar Scale after negative pressure is applied through the tissue contact layer for a period of time sufficient to close the wound, compared to if negative pressure is applied at the tissue site without using said tissue contact layer.

15. The apparatus of claim 14, wherein individual perforations comprise an average diameter of 0.025 mm to 1.5 mm.

16. The apparatus of claim 14, wherein the silicone comprises polysiloxane, polyorganosiloxane, or polydimethylsiloxane.

17. The apparatus of claim 14, wherein the combined open area of the apertures comprises about 17.5% or less of the total area of a single side of the tissue contact layer.

* * * * *